(12) United States Patent
Ehr et al.

(10) Patent No.: US 9,084,418 B2
(45) Date of Patent: Jul. 21, 2015

(54) PESTICIDE COMPOSITIONS OF MESO-SIZED PARTICLES WITH ENHANCED ACTIVITY

(75) Inventors: Robert J. Ehr, Indianapolis, IN (US);
Thomas H. Kalantar, Midland, MI (US); Lei Liu, Carmel, IN (US); Dale C. Schmidt, Midland, MI (US); Qiang Zhang, Fayetteville, AR (US); Min Zhao, Westfield, IN (US)

(73) Assignee: Dow AgroSciences LLc, Indianapolis, IN (US)

(*) Notice: Subject to any disclaimer, the term of this patent is extended or adjusted under 35 U.S.C. 154(b) by 113 days.

(21) Appl. No.: 13/197,106

(22) Filed: Aug. 3, 2011

(65) Prior Publication Data

US 2012/0035054 A1    Feb. 9, 2012

Related U.S. Application Data

(60) Provisional application No. 61/370,838, filed on Aug. 5, 2010.

(51) Int. Cl.
*A01N 25/28* (2006.01)
*A01N 25/04* (2006.01)
*A01N 25/12* (2006.01)

(52) U.S. Cl.
CPC ............... *A01N 25/28* (2013.01); *A01N 25/04* (2013.01); *A01N 25/12* (2013.01)

(58) Field of Classification Search
CPC ..... A01N 43/40; A01N 43/653; A01N 43/70; A01N 43/90; A01N 25/04; A01N 25/12; A01N 25/28
USPC .................. 424/409; 504/227, 240, 272, 273; 514/266.23, 359, 383, 384
See application file for complete search history.

(56) References Cited

U.S. PATENT DOCUMENTS

| | | | |
|---|---|---|---|
| 5,225,118 A | 7/1993 | Juang et al. | |
| 6,540,808 B2 | 4/2003 | Ma et al. | |
| 7,241,804 B1 | 7/2007 | Huchenberry et al. | |
| 2003/0138500 A1* | 7/2003 | Parker et al. | 424/705 |
| 2004/0091546 A1* | 5/2004 | Johnson et al. | 424/501 |
| 2005/0271735 A1 | 12/2005 | Stover et al. | |
| 2007/0020304 A1 | 1/2007 | Tamarkin et al. | |
| 2007/0196413 A1* | 8/2007 | Stern et al. | 424/417 |
| 2008/0213326 A1 | 9/2008 | Amrhein | |
| 2009/0104269 A1 | 4/2009 | Graham | |
| 2009/0238878 A1 | 9/2009 | Singh | |
| 2010/0261606 A1* | 10/2010 | Patel et al. | 504/103 |
| 2012/0035054 A1 | 2/2012 | Ehr et al. | |

FOREIGN PATENT DOCUMENTS

| | | |
|---|---|---|
| CN | 101449675 A | 6/2009 |
| WO | WO 2002/087343 | 11/2002 |
| WO | WO 03/101606 A1 | 12/2003 |
| WO | W02006015791 | 2/2006 |
| WO | W02008032328 | 3/2008 |
| WO | WO 2009/153231 | 12/2009 |
| WO | WO2011017480 A2 | 2/2011 |

OTHER PUBLICATIONS

Gonzalez-Melendi, P. et al., "Nanoparticles as smart treatment-delivery systems in plants: Assessment of different techniques of microscopy for their visualization in plant tissues," Annals of Botany, Academic Press, Jan. 2008, pp. 187-195, vol. 101, No. 1, London, GB.
Corredor, Eduardo et al., "Nanoparticle penetration and transport in living pumpkin plants: in situ subcellular identification," BMC Plant Biology, Biomed Central, Apr. 2009, p. 45, vol. 9, No. 1, London, GB.
Montasser et al., "The effect of monomers on the formulation of polymeric nanocapsules based on polyureas and polyamides," International Journal of Pharmaceutics, Nov. 2006, pp. 176-179, 335 (2007).
Boehm et al., "Poly E-caprolactone nanoparticles containing a poorly soluble pesticide: formulation and stability study," J. Microencapsulation, 2000, pp. 195-205, vol. 17, No. 2.
Liu et al., "Stabilized polymeric nanoparticles for controlled and efficient release of bifenthrin," Pest Management Science, Mar. 25, 2008, pp. 808-812, 64.
Extended European Search Report for EP 11815244.6-1454 based on PCT/US2011/046374, European Patent Office, dated Nov. 27, 2013.
Thomas Eichert, et al., "Size Exclusion Limits and Lateral Heterogeneity of the Stomatal Folia Uptake for Aqueous Solutes and Water-susupended Nanoparticles," Physiologia Plantarum, vol. 134, No. 1, Sep. 1, 2008, p. 151-160.
C.J. Tonkin, "Using Adjuvants, Surfactants, and Oils with Herbicides," Weed Control in Winter Crops 2002, May 27, 2009, pp. 1-4.
International Search Report issued by the USPTO, dated Dec. 23, 2011, for International Application No. PCT/US2011/046374, 2 pages.
International Preliminary Report on Patentability, dated Feb. 5, 2011, for International Application No. PCT/US2011/046374, 5 pages.

* cited by examiner

*Primary Examiner* — Janet Epps-Smith
*Assistant Examiner* — Courtney Brown
(74) *Attorney, Agent, or Firm* — C. W. Arnett; Faegre Baker Daniels LLP

(57) ABSTRACT

The present disclosure relates to pesticide compositions consisting of meso-sized particles in combination with certain adjuvants such as built-in adjuvants which are added directly to the formulation or to an aqueous dilution of the formulation such as tank-mix adjuvants, to provide enhanced effectiveness for the control of agricultural pests. Mesoparticle compositions containing such adjuvants have been found to provide improved effectiveness compared to mesoparticle compositions not containing such adjuvants or to conventional formulations.

19 Claims, 11 Drawing Sheets

FIGURE 1

|  | 20% Glycine-Na | 20% Glycine-K | 25% L-lysine | 37.5% L-lysine-Na | 37.5% L-lysine-K |
|---|---|---|---|---|---|
| Glycine | 12.8 g | 12.0 g | - | - | - |
| L-Lysine | - | - | 25 g | 6.00 g | 6.00 g |
| 5 N Sodium Hydroxide in Water | 33.9 g | - | - | 8.20 g | - |
| 45 wt.% Potassium Hydroxide in Water | - | 16.6 g | - | - | 5.13 g |
| Water | 17.3 g | 31.4 g | 75 g | 1.80 g | 4.89 g |

FIGURE 2

|  | Formulation Designation | |
|---|---|---|
|  | 3-4 | 617A |
| *Combine Oil Phase* | | |
| Fenbuconazole | 0.22 g | 0.70 g |
| Benzyl Acetate | 2.85 g | 6.75 g |
| Hexadecane | 0.15 g | 0.36 g |
| PAPI™ 27 polymeric MDI[1] | 0.81 g | 4.22 g |
| *Surfactant Addition* | | |
| Sodium Dodecyl Sulfate | 0.020 | 0.36 g |
| *Water Addition* | | |
| Water | 35.8 g | 28.1 g |
| *Glycine Addition* | | |
| 20% Glycine-Na | 0.22 g | - |
| *Crosslinker Addition* | | |
| 25% L-lysine | - | 8.25 g |
| 37.5% L-lysine-Na | 0.94 g | - |
| | | |
| Particle Volume Average Diameter | 107 nm | 144 nm |

[1] PAPI™ 27 (The Dow Chemical Company)

FIGURE 3

| Meso-capsule Suspension Components | | Sample | | |
|---|---|---|---|---|
| Ingredient Type | Ingredient[1] | 14 (wt %) | 15 (wt %) | 16B (wt %) |
| Active Ingredient | 328255-92-1 | 1.80 | | |
| Active Ingredient | fluroxypyr-mephyl | | | 5.73 |
| Active Ingredient | epoxyconazole | | 1.40 | |
| Solvent | acetophenone | | 17.30 | |
| Solvent | cyclohexanone | 15.79 | | |
| Solvent | Aromatic 200 | 6.77 | 6.00 | 13.69 |
| 1st Monomer | PAPI™ 27 | 6.45 | 6.45 | 5.08 |
| 2nd Monomer | L-lysine | 3.52 | 3.52 | 2.77 |
| Hydrophobe | Indopol™ H15 | 0.97 | 0.97 | 0.76 |
| Dispersant | sodium lauryl sulfate | 0.97 | 0.97 | 0.76 |
| Biocide | Proxel™ GXL | 0.10 | 0.10 | 0.10 |
| Water Balance | water | 63.63 | 63.29 | 71.11 |
| | total | 100.00 | 100.00 | 100.00 |
| Particle Volume Average Diameter (nm) | | 344 | 250 | 306 |

[1] PAPI™ 27 (The Dow Chemical Company); Indopol™ H15 (INEOS Oligomers);

Proxel™ GXL (Arch UK Biocides, Ltd.).

FIGURE 4

| | Formulation Designation | |
|---|---|---|
| | 1-6 | 1-10 |
| Penbuconazole, g | 3.975 | 0.663 |
| Surfactant | Sodium Dodecyl Sulfate | Sodium Dodecyl Sulfate |
| Surfactant (g) | 0.336 | 0.5 |
| Vol. deionized water (mL) | 67.66 | 92.5 |
| Ultrahydrophobe | n-hexadecane | n-hexadecane |
| Ultrahydrophobe (mL) | 0.49 | 0.19 |
| Monomer[1] | MMA | MMA |
| Monomer (mL) | 26.33 | 4.21 |
| Co-monomer[1] | AA | AA |
| Co-monomer (g/mL) | 0.47 | 0.15 |
| Initiator | AIBN | AIBN |
| Initiator (g) | 0.396 | 0.066 |
| Dye monomer | Dye (orange 240) | Dye (orange 240) |
| Dye monomer (g) | 0.015 | 0.003 |
| Ultrasonication time @ 450 Watts, minutes | 6 | 8 |
| Polymerization Temp., °C | 75 | 75 |
| Polymerization Time, h | 1.5 | 1.5 |
| Particle Volume Average Diameter (nm) | 105 | 74 |

[1] MMA is methyl methacrylate monomer; AA is acrylic acid co-monomer

FIGURE 5

|  | Formulation Designation | |
|---|---|---|
| Ingredients[1] | 68B | 68A |
| AI | 328255-92-1 | epoxiconazole |
| AI, g | 0.8 | 1.0 |
| 20% Pluronic™ P105, g | 1.5 | 1.5 |
| Morwet™ D425, g | 0.2 | 0.2 |
| deionized water, g | 7.2 | 7.2 |
| Dow Corning™ Antifoam B, g | 0.1 | 0.1 |
| AI final concentration, wt% | 8 | 10 |
| Particle Volume Average Diameter (nm) | 242 | 237 |

[1]Pluronic™ P105 (BASF Corporation); Morwet™ D425 (AkzoNobel); Dow Corning™ Antifoam B (Dow Corning Corporation)

FIGURE 6

| Sample | Active ingredient | Formulation type | Weight % active |
|---|---|---|---|
| 1-6 | Fenbuconazole | Latex meso-matrix | 3.72 |
| 1-10 | Fenbuconazole | Latex meso-matrix | 0.49 |
| 3-4 | Fenbuconazole | Polyurea mesocapsule | 0.54 |
| 617A | Fenbuconazole | Polyurea mesocapsule | 0.99 |
| Standard | Fenbuconazole | Wettable powder | 75 |
| 14 | 328255-92-1 | Polyurea mesocapsule | 1.8 |
| 68B | 328255-92-1 | Meso-homogeneous | 8 |
| 68A | Epoxiconazole | Meso-homogeneous | 10 |
| 15 | Epoxiconazole | Polyurea mesocapsule | 1.4 |
| 76A | Pyroxsulam | Meso-homogeneous | 10.0 |
| 70A | Atrazine | Meso-homogeneous | 10.0 |
| 16B | Fluroxypyr-meptyl | Polyurea mesocapsule | 5.7 |

FIGURE 7

| Formulation number | Type of meso-particle | Rate g ai/ha | Curative test | Expected Curative % Control with no enhancement | Protectant test | Expected Protectant % Control with no enhancement |
|---|---|---|---|---|---|---|
| 1-6 | Latex matrix particle | 125 | 43 | | 100 | |
| 1-6 | | 41.4 | 9 | | 100 | |
| 1-6 | | 13.8 | 21 | | 98 | |
| 1-6 | | 4.6 | 0 | | 60 | |
| 1-6 | | 1.5 | 2 | | 19 | |
| 1-6 plus Uptake | Latex matrix particle | 125 | 100 | 43 | 99 | 100 |
| 1-6 plus Uptake | | 41.4 | 100 | 9 | 100 | 100 |
| 1-6 plus Uptake | | 13.8 | 100 | 21 | 98 | 98 |
| 1-6 plus Uptake | | 4.6 | 94 | 0 | 95 | 60 |
| 1-6 plus Uptake | | 1.5 | 82 | 2 | 94 | 19 |
| 1-10 | Latex matrix particle | 125 | 82 | | 100 | |
| 1-10 | | 41.4 | 61 | | 100 | |
| 1-10 | | 13.8 | 0 | | 97 | |
| 1-10 | | 4.6 | 0 | | 63 | |
| 1-10 | | 1.5 | 0 | | 77 | |
| 1-10 plus Uptake | Latex matrix particle | 125 | 100 | 82 | 100 | 100 |
| 1-10 plus Uptake | | 41.4 | 96 | 61 | 100 | 100 |
| 1-10 plus Uptake | | 13.8 | 99 | 0 | 100 | 97 |
| 1-10 plus Uptake | | 4.6 | 100 | 0 | 100 | 63 |
| 1-10 plus Uptake | | 1.5 | 85 | 0 | 99 | 77 |
| 3-4 | Polyurea capsule | 125 | 98 | | 100 | |
| 3-4 | | 41.4 | 88 | | 100 | |
| 3-4 | | 13.8 | 83 | | 100 | |
| 3-4 | | 4.6 | 49 | | 99 | |
| 3-4 | | 1.5 | 9 | | 88 | |
| 3-4 plus Uptake | Polyurea capsule | 125 | 100 | 98 | 100 | 100 |
| 3-4 plus Uptake | | 41.4 | 100 | 88 | 100 | 100 |
| 3-4 plus Uptake | | 13.8 | 96 | 83 | 100 | 100 |
| 3-4 plus Uptake | | 4.6 | 100 | 49 | 100 | 99 |
| 3-4 plus Uptake | | 1.5 | 99 | 9 | 100 | 88 |
| 617A | Polyurea capsule | 125 | 70 | | 100 | |
| 617A | | 41.4 | 67 | | 100 | |
| 617A | | 13.8 | 23 | | 100 | |
| 617A | | 4.6 | 11 | | 88 | |
| 617A | | 1.5 | 27 | | 46 | |
| 617A plus Uptake | Polyurea capsule | 125 | 100 | 70 | 100 | 100 |
| 617A plus Uptake | | 41.4 | 100 | 67 | 100 | 100 |
| 617A plus Uptake | | 13.8 | 100 | 23 | 100 | 100 |
| 617A plus Uptake | | 4.6 | 100 | 11 | 100 | 88 |
| 617A plus Uptake | | 1.5 | 95 | 27 | 100 | 46 |
| Uptake | | | 0 | 0 | 0 | 0 |
| Untreated plants | | | 0 | 0 | 0 | 0 |

The disease level measured on untreated plants in curative and protectant tests was about 82 and 95 %, respectively. Uptake™ (Dow AgroSciences, LLC).

FIGURE 8

| Results of factorial analysis across rates | | | | |
|---|---|---|---|---|
| Formulation | % disease in curative test | Enhancement ratio | % disease in protectant test | Enhancement ratio |
| 1-6 - no Uptake Oil | 72 | | 29.3 | |
| 1-6 - with Uptake Oil | 4 | 18 | 2 | 14.7 |
| 1-10 - no Uptake Oil | 61.6 | | 14.8 | |
| 1-10 - with Uptake Oil | 3.2 | 19.2 | 0.1 | 148 |
| 617A - no Uptake Oil | 49.6 | | 15.6 | |
| 617A - with Uptake Oil | 0.8 | 62 | 0 | >156 |
| 3-4 - no Uptake Oil | 28.5 | | 3 | |
| 3-4 - Uptake Oil | 0.6 | 47.5 | 0 | >30 |
| Fenbuconazole 75WP (standard formulation) no Uptake Oil | 67 | | 13 | |
| Fenbuconazole 75WP (standard formulation) with Uptake Oil | 8 | 8.4 | 4.7 | 2.8 |

Uptake™ (Dow AgroSciences, LLC)

FIGURE 9

| Formulation number | Type | Rate g ai/ha | Protectant test | Expected Protectant % Control with no enhancement |
|---|---|---|---|---|
| 14 | meso-capsule | 69.2 | 94 | |
| 14 | | 20.8 | 32 | |
| 14 | | 6.9 | 16 | |
| 14 plus Uptake Oil | meso-capsule | 69.2 | 98 | 94 |
| 14 plus Uptake Oil | | 20.8 | 83 | 32 |
| 14 plus Uptake Oil | | 6.9 | 29 | 16 |
| Uptake Oil | | 0 | 0 | |
| Untreated plants | | 0 | 0 | |

Uptake™ (Dow AgroSciences, LLC)

FIGURE 10

| Formulation number | Type | Rate g ai/ha | Protectant test | Expected Protectant % Control with no enhancement |
|---|---|---|---|---|
| 68B | meso- | 6.9 | 99 | |
| 68B | homogeneous | 2.3 | 80 | |
| 68B | particle | 0.77 | 56 | |
| 68B plus Uptake | meso- | 6.9 | 100 | 99 |
| 68B plus Uptake | homogeneous | 2.3 | 100 | 83 |
| 68B plus Uptake | particle | 0.77 | 96 | 63 |
| Uptake Oil | | 0 | 17 | |
| Untreated plants | | 0 | 0 | |

Uptake™ (Dow AgroSciences, LLC)

FIGURE 11

| Formulation number | Type | Rate (ppm) | Curative test % Control | Expected Curative % Control with no enhancement |
|---|---|---|---|---|
| 14 | | 62.5 | 0 | |
| 14 | | 20.8 | 0 | |
| 14 | meso-capsule | 6.9 | 0 | |
| 14 plus Uptake Oil | | 62.5 | 86 | 0 |
| 14 plus Uptake Oil | | 20.8 | 87 | 0 |
| 14 plus Uptake Oil | meso-capsule | 6.9 | 72 | 0 |
| 14 plus Trycol 5941 | | 62.5 | 76 | 0 |
| 14 plus Trycol 5941 | | 20.8 | 75 | 0 |
| 14 plus Trycol 5941 | meso-capsule | 6.9 | 72 | 0 |
| 15 | | 6.9 | 92 | |
| 15 | | 2.3 | 87 | |
| 15 | meso-capsule | 0.8 | 91 | |
| 15 plus Uptake Oil | | 6.9 | 100 | 92 |
| 15 plus Uptake Oil | | 2.3 | 100 | 87 |
| 15 plus Uptake Oil | meso-capsule | 0.8 | 100 | 91 |
| 68A | meso- | 6.9 | 99 | |
| 68A | homogeneous | 2.3 | 86 | |
| 68A | particle | 0.8 | 94 | |
| 68A plus Emery Emgard | meso- | 6.9 | 100 | 99 |
| 68A plus Emery Emgard | homogeneous | 2.3 | 98 | 86 |
| 68A plus Emery Emgard | particle | 0.8 | 96 | 94 |
| Uptake Oil | | | 0 | |
| Trycol 5941 | | | 0 | |
| Emery Emgard | | | 0 | |
| Untreated plants | | | 0 | |

Uptake™ (Dow AgroSciences, LLC); Trycol ®5941(Cognis Corporation); Emery Emgard (an 85:15 wt% blend of Agnique ME 181-u (formerly known as Emery 2301; Cognis Corporation) and Emgard 2033 (Cognis Corporation)).

FIGURE 12

| Formulation number | Type | Rate (g ai/ha) | Protectant test | Expected Protectant % Control with no enhancement |
|---|---|---|---|---|
| 14 | | 6.9 | 71 | |
| 14 | | 2.3 | 60 | |
| 14 | meso-capsule | 0.8 | 48 | |
| 14 plus Trycol 5941 | | 6.9 | 98 | 78 |
| 14 plus Trycol 5941 | | 2.3 | 95 | 70 |
| 14 plus Trycol 5941 | meso-capsule | 0.8 | 95 | 61 |
| 15 | | 2.3 | 88 | |
| 15 | meso-capsule | 0.8 | 75 | |
| 15 plus Uptake Oil | | 2.3 | 98 | 93 |
| 15 plus Uptake Oil | meso-capsule | 0.8 | 96 | 86 |
| Uptake Oil | | | 45 | |
| Trycol 5941 | | | 25 | |
| Untreated plants | | | 0 | |

Uptake™ (Dow AgroSciences, LLC); Trycol ®5941 (Cognis Corporation)

FIGURE 13

| Formulation number | Type | Rate (g ai/ha) | Curative test | Expected Curative % Control with no enhancement |
|---|---|---|---|---|
| 14 | | 62.5 | 45 | |
| 14 | | 20.8 | 40 | |
| 14 | meso-capsule | 6.9 | 26 | |
| 14 plus Uptake Oil | | 62.5 | 98 | 53 |
| 14 plus Uptake Oil | | 20.8 | 98 | 48 |
| 14 plus Uptake Oil | meso-capsule | 6.9 | 98 | 36 |
| 14 plus Trycol 5941 | | 62.5 | 98 | 45 |
| 14 plus Trycol 5941 | | 20.8 | 96 | 40 |
| 14 plus Trycol 5941 | meso-capsule | 6.9 | 98 | 26 |
| 15 | | 2.3 | 89 | |
| 15 | meso-capsule | 0.8 | 89 | |
| 15 plus Uptake Oil | | 2.3 | 98 | 91 |
| 15 plus Uptake Oil | meso-capsule | 0.8 | 97 | 91 |
| 68A | meso-homogeneous particle | 2.3 | 96 | |
| 68A | meso-homogeneous particle | 0.8 | 94 | |
| 68A plus Emery Emgard | meso-homogeneous particle | 2.3 | 99 | 96 |
| 68A plus Emery Emgard | meso-homogeneous particle | 0.8 | 97 | 94 |
| Uptake Oil | | | 14 | |
| Trycol 5941 | | | 0 | |
| Emery Emgard | | | 0 | |
| Untreated plants | | | 0 | |

Uptake™ (Dow AgroSciences, LLC); Trycol ®5941(Cognis Corporation); Emery Emgard (an 85:15 wt% blend of Agnique ME 181-u (formerly known as Emery 2301; Cognis Corporation) and Emgard 2033 (Cognis Corporation)).

FIGURE 14

| Treatment | Herbicide Rate (g ai/ha) | Additive rate (% v/v) | AVEFA Wild Oats | ALOMY Black grass | AMARE Redroot Pigweed | EPHHL Wild Poinsettia | ABUTH Velvet leaf | POLCO Wild buck wheat | CHEAL Common Lamb-squarters | VIOAR Field Violet | STEME Common Chick weed |
|---|---|---|---|---|---|---|---|---|---|---|---|
| Pyroxsulam, 76A | 1.17 | 0 | 0 | 15 | 88 | 8 | 0 | 50 | 30 | 13 | 30 |
| Pyroxsulam, 76A plus Agral 90 | 1.17 | 0.25 | 72 | 92 | 93 | 58 | 5 | 93 | 80 | 93 | 93 |
| Pyroxsulam, 76A plus COC | 1.17 | 2 | 70 | 95 | 100 | 50 | 0 | 100 | 77 | 92 | 100 |
| Atrazine, 70A | 560 | 0 | 20 | 10 | 70 | 20 | 10 | 5 | 100 | 20 | 60 |
| Atrazine, 70A plus Agral 90 | 560 | 0.25 | 38 | 100 | 100 | 50 | 25 | 100 | 100 | 58 | 89 |
| Atrazine, 70A plus COC | 560 | 2 | 50 | 100 | 100 | 50 | 25 | 100 | 100 | 77 | 86 |
| Fluroxypyr-meptyl, 16B | 100[c] | 0 | NT | NT | 35 | 25 | 25[a] | 60[b] | 8 | 77 | 33 |
| Fluroxypyr-meptyl, 16B plus Agral 90 | 100[c] | 0.25 | NT | NT | 65 | 75 | 65[a] | 75[b] | 28 | 92 | 85 |
| Fluroxypyr-meptyl, 16B plus COC | 100[c] | 2 | NT | NT | 60 | 50 | 75[a] | 75[b] | 83 | 94 | 98 |

NT = Not Tested; [a] = Fluroxypyr-meptyl rate is 50 g ai/ha; [b] = Fluroxypyr-meptyl rate is 25 g ai/ha;

[c] = Fluroxypyr-meptyl rate is 100 grams acid equivalent / ha (gae/ha); Agral 90 (Norac Concepts Inc.);

COC = crop oil concentrate (Agri-dex, Helena Chemical Co.).

PESTICIDE COMPOSITIONS OF MESO-SIZED PARTICLES WITH ENHANCED ACTIVITY

CROSS REFERENCE TO RELATED APPLICATIONS

This application claims the benefit of U.S. Provisional Patent Application Ser. No. 61/370,838 filed Aug. 5, 2010, which is expressly incorporated by reference herein.

FIELD OF THE INVENTION

Various aspects related to pesticide compositions with enhanced activity consisting of meso-sized particles combined with adjuvants, penetrant adjuvants, oils or blends thereof and methods of their preparation and use are described.

BACKGROUND

Modern agricultural pesticide active ingredients including fungicides, insecticides miticides, herbicides and safeners, as well as growth regulators and nutrients, are typically formulated as liquid or solid formulations. These formulations are designed so that they are convenient for the grower or end user to use and so that the inherent biological activity of the active ingredient is properly expressed. The purpose of various aspects and embodiments disclosed herein is to further improve the effectiveness and efficiency of the de livery and biological activity of active ingredients used in agriculture and pest management.

SUMMARY

The term "agricultural active ingredient (AI)" as used herein refers to a chemical used in agriculture, horticulture and pest management for protection of crops, plants, structures, animals and humans against unwanted organisms such as fungal and bacterial plant pathogens, weeds, insects, mites, algae, nematodes and the like. Specifically, active ingredients used for these purposes include fungicides, bactericides, herbicides, insecticides, miticides, algaecides, nemtocides and fumigants. The term "agricultural active ingredient" also includes insect repellants and attractants and pheromones, modifiers of plant physiology or structure, zoospore attractants and herbicide safeners.

The term "meso" as used herein describes particles, capsules, or droplets which have a volume-average diameter of between about 30 nanometers (nm) and about 500 nm. The term "mesoparticle" as used herein describes capsules, core-shell particles, homogeneous particles or matrix particles having a volume-average diameter of between about 30 nm and about 500 nm.

The term "core-shell particle" as used herein describes a particle with a liquid or solid core containing an agricultural active ingredient and an outer shell partially or totally encapsulating or covering the core.

The term "capsule" as used herein describes a core-shell particle with a liquid core containing an agricultural active ingredient and an outer shell partially or totally encapsulating or covering the core.

The term "matrix particle" as used herein describes a particle consisting of an agricultural active ingredient dispersed within a solid polymer matrix such as, for example, a synthetic latex polymer.

The term "homogeneous particle" as used herein describes a particle composed of from about 80% to about 99% of an agricultural active ingredient.

The term "about" means a range of plus to minus 10 percent, e.g. about 1 included values from 0.9 to 1.1.

The term "poorly water soluble" as used herein means agricultural active ingredients with solubility in water of less than about 1000 ppm. Preferably, the poorly water soluble active ingredient has solubility in water of less than 100 ppm, more preferably less than 10 ppm.

The term "water immiscible solvent" as used herein means a solvent or mixture of solvents with a solubility in water of about 10 g/100 ml or less.

The term "essentially no surfactant" as used herein means a surfactant concentration of less than 1 weight percent with respect to the oil phase and more preferably less than 0.5 wt. percent of a surfactant with respect to the oil phase.

The term "surfactant" as used herein means a substance used to create and/or stabilize an emulsion. Surfactants include nonionic, anionic, cationic, or combinations of nonionic and anionic or nonionic and cationic. Examples of suitable surfactants include alkali metal lauryl sulfates such as sodium dodecyl sulfate, alkali metal fatty acids salts such as sodium oleate and sodium stearate, alkali metal alkylbenzene sulfonates such as sodium dodecylbenzene sulfonate, polyoxyethylene nonionics, and quaternary ammonium surfactants. Standard reference sources from which one of skill in the art can select suitable surfactants, without limitation to the above mentioned classes, include Handbook of Industrial Surfactants, Fourth Edition (2005) published by Synapse Information Resources Inc, and McCutcheon's Emulsifiers and Detergents, North American and International Editions (2008) published by MC Publishing Company.

The term "adjuvant" as used herein refers to substances which can increase the biological activity of the active ingredient, but are themselves not significantly biologically active. Adjuvants assist with the effectiveness of the active ingredient such as, for example, by improving the delivery and uptake of an herbicide into a target weed plant leading to improved biological control. Adjuvants, in the form of solids or liquids, can be incorporated directly into the formulation of an agricultural active ingredient or it can be added to an aqueous dilution of the formulated agricultural active ingredient to provide improved performance of the product upon application. Commonly used adjuvants may include, for example, surfactants, spreaders, penetrants, petroleum and plant derived oils and solvents and wetting agents. Examples of commonly used adjuvants include, but are not limited to, paraffin oil, horticultural spray oils (e.g., summer oil), methylated rape seed oil, methylated soybean oil, highly refined vegetable oil and the like, polyol fatty acid esters, polyethoxylated esters, ethoxylated alcohols, ethoxylated phenols such as nonylphenol ethoxylates, alkyl polysaccharides and blends, amine ethoxylates such as Ethomeen T/25™ and Armoblend AB600™ (Akzo-Nobel), sorbitan fatty acid esther ethoxylates, polyethylene glycol esters such as PEG (Huntsman) and Polyglycol 26-2™ (The Dow Chemical Co), organosilicone based surfactants such as Boost (Dow AgroSciences, LLC), ethylene vinyl acetate terpolymers, ethoxylated alkyl aryl phosphate esters such as Lubrol 17A17™ and Atlox MBA 13/10™ (Uniqema) and Rhodafac RS610™ (Rhodia) and the like. These and other adjuvants are described in the "Compendium of Herbicide Adjuvants, 9th Edition," edited by Bryan Young, Dept. of Plant, Soil and Agricultural Systems, Southern Illinois University MC-4415, 1205 Lincoln Drive, Carbondale, Ill. 62901, which is available for viewing on the internet at http://www.herbicide-adjuvants.com/. In addition, the *Handbook of Industrial Surfactants* and McCutcheon's *Emulsifiers and Detergents*, as cited herein, are two additional sources for some of the adjuvant types described herein.

The term "penetrant" as used herein refers to materials that enhance the ability of a agricultural active ingredient to penetrate into or through the surface of a plant. Typical penetrants are paraffinic oils, crop oils, seed oils or methylated seed oils that are able to dissolve or penetrate waxy layers on leaves. Penetrants also include these types of oils mixed with from 0.5 to about 40% emulsifiers or surfactants to further enhance their utility and effectiveness. Examples of penetrants include but are not limited to: petroleum oil concentrates such as Agri-dex™ (Helena Chemical Co), Crop Oil Concentrate (Helena Chemical Co. and others), Herbimax™ (Loveland Products Inc.), Penetrator™ (Helena Chemical Co), and Uptake™ Oil (Dow AgroSciences, LLC). Ethylated or methylated vegetable oils, such as Hasten™, (Wilbur-Ellis Company) Tronic™ (Kalo, Inc.), Renegade™ (Wilbur-Ellis Company) and modified vegetable oil, and vegetable oil concentrates such as Amigo™ (Loveland Products Inc.) and Peerless.™ (Custom Chemicides).

The term "built-in adjuvant" as used herein refers to one or more adjuvants that have been added to a particular formulation, such as a granule or liquid formulation, at the manufacturing stage of the product, rather than at the point of use of the product such as, for example, to a spray solution. The use of built-in adjuvants simplifies the use of agrochemical products for the end-user by reducing the number of ingredients that must be individually measured and applied.

The term "interfacial condensation" as used herein means a reaction between two complimentary, organic intermediates that takes place at an interface between two immiscible liquids in which one immiscible liquid is dispersed in the other immiscible liquid. An example of an interfacial condensation reaction is given by U.S. Pat. No. 3,577,515 which is expressly incorporated by reference herein. A "core-shell" capsule is a capsule created by an interfacial condensation reaction that takes place between two immiscible phases in which the first immiscible phase is a dispersed phase, the second immiscible phase is a continuous phase; and the dispersed phase or core is encapsulated within a shell formed by the reaction of two complimentary, organic intermediates which form the shell and the core-shell capsule is dispersed within the continuous phase.

The term "crosslinker" as used herein means a substance that initiates and facilitates reaction of polymer precursors to form a core shell particle. The crosslinker may or may not become part of the polymer structure comprising the core shell particle. Examples of crosslinkers as used herein include water, water-soluble diamines, water soluble polyamines, water soluble polyamino acids, water soluble diols, water soluble polyols, and mixtures thereof.

The present disclosure relates to novel pesticide compositions consisting of meso-sized particles containing AIs and certain adjuvants such as built-in adjuvants which are added directly to the formulation or to an aqueous dilution of the formulation such as tank-mix adjuvants, to provide enhanced effectiveness for the control of agricultural pests. Mesoparticle compositions containing such adjuvants have been found to provide improved biological effectiveness compared to mesoparticle compositions not containing such adjuvants or to conventional formulations. We have found that the addition of certain adjuvants, especially penetrant adjuvants to mesoparticle formulations provides even greater effectiveness than meso-particle formulations not containing adjuvants. These compositions provide improved effectiveness compared to conventional formulations of the same active ingredient. Meso-sized particles are in the size range of 30 to 500 nm and may be of diverse morphology, including, but not limited to meso-homogeneous particles comprised of substantially pure (>80%) active ingredient, meso-capsules containing active ingredient, and meso-matrix particles containing active ingredient. The present disclosure concerns formulations of meso-particles containing certain built-in adjuvants and of meso-particle formulations in diluted form mixed with certain adjuvants prior to contacting plants, and of contacting a plant at risk of insect or disease attack or an agricultural weed with these compositions so as to effectively control said pests.

One embodiment of the present disclosure includes a composition for the delivery of an agricultural active ingredient, comprising an adjuvant combined with a mesocapsule, the mesocapsule having a polymer shell, and a poorly water soluble agricultural active ingredient, wherein the active ingredient is at least partially included within the polymer shell, the mesocapsules having a volume-average particle diameter between about 30 nm and about 500 nm. The adjuvant is a built-in adjuvant comprising from 1 to about 90% of the formulation or it can be a tank-mixed comprising from 0.05 to about 5% of the dilute spray solution.

Another embodiment of the present disclosure includes a composition for the delivery of an agricultural active ingredient combined with a meso-homogeneous particle the meso-homogeneous particle being comprised of from about 80 to about 99% of a poorly water soluble agricultural active ingredient wherein the meso-homogeneous particles have a volume-average particle diameter between about 30 nm and about 500 nm. The adjuvant is a built-in adjuvant comprising from 1 to about 90% of the formulation or it can be a tank-mixed comprising from 0.05 to about 5% of the dilute spray solution.

Yet another embodiment of the present disclosure includes a composition for the delivery of an agricultural active ingredient, comprising a meso-matrix particle combined with an adjuvant, the meso-matrix particle being comprised of a poorly water soluble agricultural active ingredient, wherein the active ingredient is distributed throughout a polymer matrix, the meso-matrix particles having a volume-average particle diameter between about 30 nm and about 500 nm. The adjuvant is a built-in adjuvant comprising from 1 to about 90% of the formulation or it can be a tank-mixed comprising from 0.05 to about 5% of the dilute spray solution.

The present disclosure also embodies a method for treatment or prophylaxis of a fungal disease on plants with fungicides formulated as mesoparticles and combined with built-in or tank-mixed adjuvants, wherein the method consists of contacting a plant, plant tissue, plant cells or a seed with an agriculturally effective amount of the aforementioned compositions employing application or spray techniques known to those skilled in the art.

The present disclosure also embodies a method for treatment or prophylaxis of a insect and mites infestations on plants with insecticides and miticides formulated as mesoparticles and combined with built-in or tank-mixed adjuvants, wherein the method consists of contacting an insect, a mite, a plant, plant tissue, plant cells or a seed with an agriculturally effective amount of the aforementioned compositions employing application or spray techniques known to those skilled in the art.

The present disclosure also embodies a method for treatment or prophylaxis of weed infestations in agricultural crops with herbicides formulated as mesoparticles and combined with built-in or tank-mixed adjuvants, wherein the method consists of contacting a plant, plant tissue, plant cells or a seed with an agriculturally effective amount of the aforementioned compositions employing application or spray techniques known to those skilled in the art.

As used herein, the terms 'plant' and 'agricultural crop' shall mean any commercially propagated plant whether produced by conventional plant breeding, vegetative propagation or by employing techniques of genetic modification.

BRIEF DESCRIPTION OF THE FIGURES

FIG. 1 summarizes the components of stock solutions of glycine and lysine that were prepared and used to synthesize the exemplary mesocapsules disclosed herein.

FIG. 2 summarizes the compounds that were combined in order to synthesize the exemplary mesocapsules disclosed herein.

FIG. 3 summarizes the compounds that were combined in order to synthesize the mesocapsules containing 328255-92-1 as disclosed herein.

FIG. 4 summarizes the compounds that were combined in order to synthesize the exemplary meso-matrix latex particles disclosed herein.

FIG. 5 summarizes the compounds that were combined in order to synthesize the exemplary meso-homogeneous particles disclosed herein.

FIG. 6 includes a list of exemplary formulations of fungicides tested for their effectiveness as a fungicide; the table lists the formulations and provides an estimate of the wt. % of agricultural active ingredient (AI) in each formulation.

FIG. 7 summarizes the results of testing various formulations identified in FIG. 6 for their ability to cure and prevent Leaf Blotch disease of wheat plants caused by *Septoria tritici* in 2-day curative or 4-day protectant tests, respectively.

FIG. 8 summarizes the enhancement ratios of the various formulations identified in FIG. 6 with and without adjuvant for their ability to cure and prevent Leaf Blotch disease of wheat plants caused by *Septoria tritici* in 2-day curative or 4-day protectant tests, respectively.

FIG. 9 summarizes the results of testing mesocapsule formulations identified in FIG. 6 for their ability to prevent Brown Rust disease on wheat plants caused by *Puccinia recondita* f. sp. *Tritici* in 4-day protectant tests.

FIG. 10 summarizes the results of testing meso-homogenous formulations identified in FIG. 6 for their ability to prevent Brown Rust disease on wheat plants caused by *Puccinia recondita* f. sp. *Tritici* in 4-day protectant tests.

FIG. 11 summarizes the results of testing meso-particle formulations identified in FIG. 6 for their ability to cure and prevent Brown Rust disease on wheat plants caused by *Puccinia recondita* f. sp. *Tritici* in a 2-day curative test.

FIG. 12 summarizes the results of testing various formulations identified in FIG. 6 for their ability to prevent Leaf Blotch disease of wheat plants caused by *Septoria tritici* in a 3-day protectant test.

FIG. 13 summarizes the results of testing various formulations identified in FIG. 6 for their ability to cure Leaf Blotch disease of wheat plants caused by *Septoria tritici* in a 3-day curative test.

FIG. 14 summarizes the results of testing various formulations identified in FIG. 6 for their ability to control various weed species in postemergent spray tests.

DESCRIPTION

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

Discovering, developing and producing effective and economical agricultural active ingredients (AIs) such as fungicides, insecticides, herbicides, modifiers of plant physiology or structure, and the like is only part of the challenge facing the agriculture chemical industry. It is also important to develop effective formulations of these types of compounds to enable their efficient and economical application. Cost considerations alone dictate an ever-growing need for new formulations and methods for making and using AIs. This need is especially acute when the effectiveness of AIs is limited or when they are difficult to handle and apply effectively as desired due to problems such as low solubility in aqueous solutions, poor bioavailability in and on plants and insects or poor penetration of the plant surface.

One of the most effective ways of improving the efficacy of AIs is to increase the penetration of the AIs into the plant either through the root system or through the stem and leaf surfaces. Often times this involves formulating the AIs in a water soluble form. However, many otherwise effective AIs are not very soluble in water. Accordingly, a formulation that increases the penetration of poorly water soluble AIs into and through plants has the potential to improve overall effectiveness of a wide variety of AIs including, for example, AIs that are not very soluble in water.

Some aspects disclosed herein increase an agricultural active ingredient's bioavailability by providing the AI as a particle of very small size e.g., a mesoparticle having a volume-average particle diameter of about 500 nm or less; in some aspects the mesoparticle diameter is on the order of 300 nm or less. Some of these mesoparticles include a surface functionalized with biologically compatible hydrophilic functional groups such as carboxylic acid groups. In many applications AIs in the form of mesoparticles more effectively penetrate plants and are more efficiently transported within the plant and through the plant than are AI's that are larger than mesoparticles.

This invention consists of compositions of adjuvants and mesoparticles which include meso-sized core-shell particles, such as capsules, matrix particles and homogeneous particles. Mesoparticles of the current invention may be prepared by the methods discussed herein.

Mesocapsules can be synthesized utilizing the steps of providing an oil phase, the oil phase including at least one agricultural active ingredient and one or more polymer precursors such as a polyisocyanate capable of reacting to form a shell, supplying an aqueous phase, the aqueous phase including water and at least one crosslinker, adding a surfactant to at least one of the aqueous phase and the oil phase, mixing the oil and the aqueous phases under shear conditions sufficient to form an emulsion having meso-sized droplets with a volume-average diameter of about 500 nm or less, and reacting the polymer precursor with the crosslinker to form the mesocapsule.

Surfactant free mesocapsules can be synthesized utilizing the steps of providing an oil phase, the oil phase including at least one agricultural active ingredient and at least one polyisocyanate, supplying an aqueous phase, wherein the aqueous phase includes at least one component wherein the component includes at least one functional moiety that is either a primary or secondary amine or a primary or secondary amino group and additionally at least one hydrophilic functional group, mixing the oil and the aqueous phases to form an emulsion, and reacting polyisocyanate with a crosslinker to form the mesocapsule.

Core-shell mesocapsules can be prepared by a number of methods including interfacial polymerization at the surface of a droplet or particle or polymerization inside the dispersed phase. A preferred encapsulating polymer is polyurea including those formed from the reaction of polyisocyanate with a polyamine, a poly amino acid, or water. Other preferred encapsulating polymers include those formed from melamine-formaldehyde or urea-formaldehyde condensates, as well as similar types of aminoplasts. Capsules having shell walls comprised of polyurethane, polyamide, polyolefin, polysaccharide, protein, silica, lipid, modified cellulose, gums, polyacrylate, polyphosphate, polystyrene, and polyesters or combinations of these materials can also be used to form core-shell mesocapsules.

Suitable polymers for use in forming mesocapsules of the present disclosure include amino-based prepolymers such as urea-, melamine-, benzoguanamine-, and glycouril-formaldehyde resins and dimethyloldihydroxyethylene urea type prepolymers. These prepolymers can be used as blends and cross linkers with polyvinyl alcohol, polyvinyl amines, acrylates (acid functionality preferred), amines, polysaccharides, polyureas/urethanes, poly amino acids, and proteins. Other suitable polymers include polyesters, including biodegradable polyesters, polyamides, polyacrylates and polyacrylamides, polyvinyl polymer and copolymers with polyacrylates, polyurethanes, polyethers, polyureas, polycarbonates, naturally occurring polymers such as, polyanhydrides, polyphosphazines, polyoxazolines, and UV-cured polyolefins.

A poorly water soluble agricultural active ingredient is encapsulated within a core-shell particle of very small size e.g., of about 500 nm or less, more preferably 300 nm or less. AIs encapsulated in these mesocapsules may exhibit increased penetration into plants, plant cells and even plant pathogens than AIs that are not associated with mesocapsules and is combined with a tank-mixed or built-in adjuvant.

Mesocapsules can include hydrophilic functional groups built into the polyurea shell and at least partially exposed on the mesocapsule's surface. A partial listing of some of the functional materials that can be used to form these particles can be found in the following publication, WO2001/94001, which is incorporated herein by reference in its entirety. Hydrophilic functional groups include carboxylate, salts of carboxylate, phosphonate, salts of phosphonate, phosphate, salts of phosphate, sulfonate, salts of sulfonate, quaternary ammonium, betaine, oxyethylene or oxyethylene-containing polymers. Preferably, the hydrophilic group is a carboxylate or the salt of a carboxylate.

Some AIs are solid at room temperature and must be dissolved in a solvent before they can be encapsulated within a polyurea mesocapsule. In one example a poorly water-soluble AI is dissolved in a solvent that readily dissolves the AI before adding the oil phase. Suitable solvents may be one or a mixture of organic solvents that have low water solubility, i.e. about 10 g/100 ml or less, which includes, but are not limited to, petroleum fractions or hydrocarbons such as mineral oil, aromatic solvents, xylene, toluene, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, ethylhexyl benzoate, isopropyl benzoate, n-butyl oleate, isopropyl myristate, propylene glycol dioleate, di-octyl succinate, di-butyl adipate, di-octyl phthalate, acetyl tributyl citrate, triethylcitrate, triethyl phosphate, and the like; esters of mono, di and polycarboxylic acids, such as benzylacetate, ethylacetate, and the like; ketones, such as cyclohexanone, acetophenone, 2-heptanone, gamma-butyrolactone, isophorone, N-ethyl pyrrolidone, N-octyl pyrrolidone, and the like; alkyldimethylamides, such as dimethylamide of C8 and C10, dimethylacetamide, and the like; alcohols of low water solubility (i.e. about 10 g/100 ml or less) such as benzyl alcohol, cresols, terpineols, tetrahydrofurfurylalcohol, 2-isopropylphenol, cyclohexanol, n-hexanol, and the like. In some cases, an ultra-hydrophobe is added to the oil phase, ostensibly to preserve the stability of an emulsion that will be created later in the process when the oil phase is mixed with an aqueous phase. This additive is a highly water-insoluble material that 1) has a negligible diffusion coefficient and negligible solubility in the continuous aqueous phase and 2) is compatible with the dispersed phase. Examples of ultrahydrophobes include long chain paraffins such as hexadecane, polymers such as polyisobutene, polystyrene, polymethylmethacrylate, natural oils such as seed oils, and silicones such as silicone oil or dimethicone. Preferably, the additive is used in an amount not greater than 10 weight percent based on the weight of the dispersed phase.

The polymer precursor within the oil phase of the emulsion is a polyisocyanate. The polyisocyanate reacts with a crosslinker or with water to form a polyurea shell. Examples of polyisocyanates include but are not limited to toluene diisocyanate (TDI), diisocyanato-diphenylmethane (MDI), derivatives of MDI such as polymethylene polyphenylisocyanate that contains MDI, an example of which is PAPI™ 27 polymeric MDI (The Dow Chemical Company), isophorone diisocyanate, 1,4-diisocyanatobutane, phenylene diisocyanate, hexamethylene diisocyanate, 1,3-bis(isocyanatomethyl) benzene, 1,8-disocyanatooctane, 4,4'-methylenebis(phenyl isocyanate), and 4,4'-methylenebis(cyclohexyl isocyanate). In another example, suitable polymer precursors in the dispersed oil phase may also include but are not limited to diacid chlorides, polyacid chlorides, sulfonyl chlorides, chloroformates, and the like.

The oil and water phases are combined in the presence of a surfactant that aids in the creation and or stabilization of meso-size droplets of less than 500 nm but preferable less than 300 nm. The surfactant can be added to either the oil phase or to the water phase or to both the oil and water phases. Surfactants include nonionic, anionic, cationic, or combinations of nonionic and anionic or nonionic and cationic. Examples of suitable surfactants include alkali metal lauryl sulfates such as sodium dodecyl sulfate, alkyl metal fatty acids salts such as oleates and stearates, alkali methyl alkylbenzene sulfonates such as sodium dodecylbenzene sulfonate, polyoxyethylene nonionics, and quaternary ammonium surfactants. Standard reference sources from which one of skill in the art can select suitable surfactants, without limitation to the above mentioned classes, include Handbook of Industrial Surfactants, Fourth Edition (2005) published by Synapse Information Resources Inc, and McCutcheon's Emulsifiers and Detergents, North American and International Editions (2008) published by MC Publishing Company.

The emulsion can be prepared by a variety of methods, including batch and continuous methods well known in the art. In a preferred method, the emulsion is prepared using an ultra-high shear device such as an ultrasonicating device or a high-pressure homogenizer to create meso-size droplets of less than 500 nm, preferably less than 300 nm. Ultrasonicating devices include standard sonicating equipment containing a ultrasonic probe that is inserted into the formulation to create the meso-size droplets, one representative example being the Sonicator 400 from Misonix Sonicators. High-pressure homogenizers use very high pressure, 500 to 20,000 psi, to force fluid through a small opening and create the meso-size droplets. Examples of such devices include, but are not limited to the EmulsiFlex™ (Avestin, Inc.) devices and the Microfluidizer™ (Microfluidics) devices.

In one approach a polyisocyanate reacts with hydroxyl-containing or amine-containing molecules in the continuous phase (i.e. water), such as water-soluble diamines, water soluble polyamines, water soluble polyamino acids, water soluble diols, water soluble polyols, and mixtures thereof, via an interfacial polycondensation to form a polymeric shell. Examples of these reactive intermediates in the aqueous continuous phase may include, but are not limited to, water soluble diamines, such as ethylene diamine, and the like; water soluble polyamines, such as diethylenetriamine, triethylenetetramine, tetraethylenepentamine, pentaethylenehexamine, and the like; water soluble amino acids having more than one isocyanate-reactive functional group, such as L-lysine, arginine, histidine, serine, threonine, polymers or oligomers of these aminoacids, and the like; water soluble diols or water soluble polyols, such as ethylene glycol, propylene glycol, polyethylene oxide diol, water soluble amino alcohols, such as 2-aminoethanol, and the like. In one embodiment the water soluble phase includes a polyamine with a carboxylate functionality (such as L-lysine) which reacts to form a polyurea shell that includes carboxylate functional groups at the surface of the mesocapsule. This carboxylate functionality may be unneutralized or it may be partly or fully neutralized to form a carboxylate salt.

In still another approach the diamine or polyamines or their equivalents, included in the aforementioned exemplary aqueous phase, are omitted from the reaction mixture. In this approach the polyisocyanate reacts with water to form a polyurea shell.

Various factors can be adjusted to increase or decrease the interfacial condensation reaction rate. These factors include, for example, temperature, pH, mixing rate, reaction times, osmotic pressure and of course changing the levels and types of emulsifiers, polymer components, solvents, the addition of catalysts and the like. For an additional discussion of the effect on temperature, catalysts, pH and the like on these types of reactions see for example U.S. Pat. No. 4,285,750, which is incorporated herein by reference in its entirety. Additional information on the effect of salts and salt levels on these types of reactions can be found in publication, WO2006/092409, which is incorporated herein by reference in its entirety.

Some embodiments of the present disclosure can be realized by varying the levels of some of the reactants in the reaction mixture, the reaction mixture consisting of a dispersed oil phase and a continuous aqueous phase which are used to form mesocapsules that include at least one AI. In some embodiments these include, given as weight percent (wt. %) of the oil phase of at least one AI in the range of from about 1.0 wt. % to about 90 wt. %, more preferably from about 1.0 wt. % to about 80 wt. %; optionally, a solvent suitable for dissolving the AI in the range of from about 1 wt. % to about 90 wt. %, more preferably from about 20 wt. % to about 80 wt. %; optionally, an ultrahydrophobe present in the range of from about 0.5 wt. % to about 10 wt. %, more preferably from about 1.0 wt. % to about 5.0 wt. %; at least one polyisocyanate present in the range of from about 1 wt. % to about 30 wt. %, more preferably from about 5 wt. % to about 20 wt. %; optionally, an emulsifier present in the range of from 0.1 wt. % to about 20 wt. %, more preferably from about 1 wt. % to about 10 wt. % of the oil phase, in which the oil phase makes up on the order of from about 1% to about 60% of the total amount of the emulsion.

The aqueous phase of the reaction mixture consists of from about 40 wt. % to about 99 wt. % of the total emulsion and contains from about 60 wt. % to about 90 wt. % water, from about 1 wt. % to about 30 wt. % of one or more cross-linkers and optionally, from about 0.1 wt. % to about 20 wt. % of one or more water soluble surfactants.

Some of the ingredients used in some of the exemplary formulations are optional. For example, it is possible to synthesize mesocapsules in some instances without adding the solvent and/or the ultrahydrophobe. The addition of these types of optional components to the reaction mixture is especially useful when the AI is a solid.

As described herein, one method used in encapsulating poorly water-soluble materials is to create a polyurea core-shell by interfacial condensation reaction of a polyisocyanate in the oil phase which reacts with at least one of water and with a water-soluble polyamine in the continuous phase. In order to stabilize the microcapsule against agglomeration and to control the size of microcapsule before the reaction, it is often desirable to add one or more surfactants or colloidal stabilizers to the reaction mixture. A surfactant may be useful if the goal of the reaction is to create mesocapsules smaller than 500 nm. However, the presence of surfactant may be detrimental in many end use applications. For example, in delivery of agricultural active ingredients into a plant, the surfactant accompanying the polyurea mesocapsules may be toxic to the plant. In other applications, the surfactant may also cause unwanted foaming in the final product. Accordingly, it may be beneficial to develop a method for efficiently synthesizing micro- and mesocapsules that required less or no surfactant than the methods previously discussed.

One aspect of the method for producing mesocapsules in which a compound is added that includes at least one functional moiety that is either a primary or secondary amine or a primary or secondary amino group and additionally at least one hydrophilic functional group, and wherein the addition of this component allows for an emulsion to be made with essentially no surfactant. In one variation of this method, the component is glycine, a salt of glycine, or a mixture of glycine and a salt of glycine. These methods for producing micro- or mesocapsules include adding glycine, a salt of glycine, or a mixture of glycine and a salt of glycine to the aqueous phase of the reaction mixture before creating the final emulsion, and, if desired, before initiating the cross linking reaction between components such as polyisocyanate to create the polyurea mesocapsules shell. Additional molecules that can be used in addition to or in place of glycine include other molecules that have either a primary or secondary amine group on one end and of the molecule and a hydrophilic group such as a carboxylate or a trimethylamine on the other end of the molecule. It may not be necessary to neutralize all of the charged moieties in order to obtain the product formed by the processes disclosed herein. It may be that adding either the glycine, a glycine salt, or a glycine-like material before forming the final emulsion allows the glycine to react with a small part of the di- or polyisocyanate to create a surfactant-like molecule which aids in the creation and/or the stabilization of the emulsion and helps control the droplet size in the final emulsion. Next, after creation of the final emulsion, during the interfacial condensation reaction, the surfactant-like molecule formed by the reaction of glycine reacts to become incorporated into the polyurea shell and no longer acts as a free surfactant. The hydrophilic functional group of the glycine or glycine like molecule exists at the surface of the shell to help stabilize the shell. A partial list of some of these types of molecules can be found in U.S. Pat. No. 4,757,105 which is incorporated herein by reference in its entirety.

Polyurea meso-capsules can be made without surfactant using colloidal stabilizers such as polyvinyl alcohol but it is difficult to control particle size. Some formulations of AIs are made using surfactants that do not exhibit some of the properties that need to be avoided, such as using less phytotoxic surfactants or surfactants that exhibit less foaming.

Adding a glycine salt or a similar molecule that includes either primary or secondary amine groups and either a carboxylate group or a trimethylamine to the aqueous phase before creating the final emulsion lowers or eliminates altogether the need to add a surfactant to the reaction mixture. Adding a material that is not a surfactant such as glycine and that reacts with the di- or polyisocyanate to create a molecule that helps to emulsify and stabilize the organic phase and that further reacts into polyurea shell once the di or polyisocyanate, enables the production of mesocapsules that are free or essentially free of surfactants. In some embodiments essentially free implies that the oil phase includes less than about 1.0 wt % and more preferably less than 0.5 wt. percent of a surfactant.

Being able to formulate mesocapsules that include no or very little residual surfactant has advantages in many applications where the presence of free surfactant in the formulation has a detrimental or unwanted effect. There may also be a potential cost advantage in case the amount of expensive surfactant can be reduced.

An exemplary method of forming the mesocapsules includes an interfacial polycondensation reaction between the AI in the oil phase and either water or a water soluble cross linker in the aqueous phase. In order to produce mesocapsules, especially mesocapsules with an average diameter of about 500 nm or less or mesocapsules with an average diameter of about 300 nm or less, either a surfactant such as sodium dodecyl sulfate can be added to the reaction mixture or a molecule such as glycine can be added to the aqueous phase before creating the final emulsion and/or initiating the cross linking reaction. In one variation the oil and aqueous phases are mixed under high-shear to form an emulsion that includes meso-sized droplets which are converted into polyurea meso-capsules as described herein. Devices for processing the emulsion to help form mesocapsules include ultrasonicating devices and/or high-pressure homogenizers. Ultrasonicating devices include standard sonicating equipment containing a ultrasonic probe that is inserted into the system to create the meso-size droplets, one representative example being the Sonicator 400 from Misonix Sonicators. High-pressure homogenizers use very high pressure, 500 to 20,000 psi, to force fluid through a small opening and create the meso-size droplets. Examples of such devices include the EmulsiFlex™ (Avestin, Inc.) devices and the Microfluidizer™ (Microfluidics) devices.

In another variation an AI with a low solubility in water is optionally dissolved in a solvent such as benzyl acetate. Optionally, an ultrahydrophobe such as hexadecane can be added to help preserve the stability of an emulsion that will form once the oil and water phases are combined. A polyisocyanate, for example PAPI™ 27 polymeric MDI (The Dow Chemical Company), is added to the oil phase. In order to aid in the formation of meso-sized droplets which are a precursor to forming mesocapsules, a surfactant such as the sodium salt of dodecyl sulphate (SDS) may be added to either or both the oil or water phases. Alternatively, glycine or any other molecule with either an amine or amino moiety on one end of the molecule and a hydrophilic group on the other end of the molecule is added to the aqueous phase before forming the final emulsion or initiating the cross-linking reaction. The amount of glycine or similar molecule can be increased as necessary to replace all or at least some of the surfactant. The oil and water phases are mixed and optionally processed with an ultra-high shear device such as a Microfluidizer™ (Microfluidics) device to create the desired small droplets which are converted into polyurea mesocapsules as described herein.

Meso-matrix particles can be prepared by utilizing the steps of providing an oil phase, the oil phase including at least one agricultural active ingredient, an initiator, a monomer, a co-monomer, an optional dye monomer, and an ultrahydrophobe, supplying an aqueous phase, the aqueous phase including water and a surfactant, mixing the oil and the aqueous phases under shear conditions sufficient to form an pre-emulsion and then sonicating the pre-emulsion to produce the meso-sized droplets with a volume-average diameter of about 500 nm or less, and finally polymerizing the monomers within the droplets by heating the emulsion to form the polymer matrix containing the AI which constitutes the meso-matrix particles. In general, the procedures used for preparing the emulsion of meso-sized droplets can be similar to those for the preparation of the meso-capsules, as described above, as will be apparent to those proficient in the art. The AI level in the meso-matrix particle can be from about 1 to about 80 wt %, of the meso-matrix particle weight on a dry weight basis.

Suitable initiators (including controlled growth free radical initiator systems), ultrahydrophobes, dispersing agents and surfactants, shear dispersing procedures and equipment, polymerization conditions, and monomers and co-monomers for use in the preparation of meso-matrix particles of the present disclosure are described in, for example, but not limited to those described in US 2006/0052529 A1 (Mar. 9, 2006), U.S. Pat. No. 5,686,518 (Nov. 11, 1997), and U.S. Pat. No. 6,710,128 B1 (Mar. 23, 2004), U.S. Pat. No. 7,317,050 B2 (Jan. 8, 2008), US 2002/0032242 A1 (May 16, 2001), and US 2006/0223936 A1 (Dec. 20, 2002). General methods for the preparation of meso-sized emulsions and polymerization of said emulsions are described, for example, by M. Antonietti and K. Landfester in "Polyreactions in miniemulsions," *Progress in Polymer Science*, vol. 27(4), pages 689-757 (2002), and by M. S. El-aasser, C. D. Lack, Y. T. Choi, T. I. Min, J. W. Vanderhoff and F. M. Fowkes in "Interfacial aspects of miniemulsions and miniemulsion polymers," *Colloids and Surfaces*, vol. 12, page 79 (1984).

Meso-homogeneous particles can be prepared by utilizing the steps of providing an aqueous phase, the aqueous phase including at least one agricultural active ingredient, a surfactant, a wetting agent and water, and ball milling the aqueous phase utilizing suitable equipment and conditions that are well known to those of normal skill in the art until the meso-homogeneous particles with a volume-average diameter of about 500 nm or less are formed.

In one embodiment, the agricultural active ingredient is at least one agricultural chemical selected from the group consisting of fungicides, bactericides, herbicides, insecticides, miticides, algaecides, nemtocides, insect attractants and pheromones, modifiers of plant physiology or structure, zoospore attractants and herbicide safeners.

In one embodiment, the mesoparticle contains an agricultural active ingredient has solubility in water on the order of about 1,000 parts per million or less, preferably 100 parts per million or less, and more preferably 10 parts per million or less.

Many classes and types of insecticides are useful in agriculture. Examples include insecticides such as antibiotic insecticides such as allosamidin and thuringensin; macrocyclic lactone insecticides such as spinosad, spinetoram and 21-butenyl spinosyns; avermectin insecticides such as abamectin, doramectin, emamectin, eprinomectin, ivermectin and selamectin; milbemycin insecticides such as lepimectin, milbemectin, milbemycin oxime and moxidectin; botanical insecticides such as anabasine, azadirachtin, d-limonene, nicotine, pyrethrins, cinerins, cinerin I, cinerin II, jasmolin I, jasmolin II, pyrethrin I, pyrethrin II, quassia, rotenone, ryania and sabadilla; carbamate insecticides such as bendiocarb and carbaryl; benzofuranyl methylcarbamate insecticides such as benfuracarb, carbofuran, carbosulfan, decarbofuran and furathiocarb; dimethylcarbamate insecticides dimitan, dimetilan, hyquincarb and pirimicarb; oxime carbamate insecticides such as alanycarb, aldicarb, aldoxycarb, butocarboxim, butoxycarboxim, methomyl, nitrilacarb, oxamyl, tazimcarb, thiocarboxime, thiodicarb and thiofanox; phenyl methylcarbamate insecticides such as allyxycarb, aminocarb, bufencarb, butacarb, carbanolate, cloethocarb, dicresyl, dioxacarb, EMPC, ethiofencarb, fenethacarb, fenobucarb, isoprocarb, methiocarb, metolcarb, mexacarbate, promacyl, promecarb, propoxur, trimethacarb, XMC and xylylcarb; dinitrophenol insecticides such as dinex, dinoprop, dinosam and DNOC; fluorine insecticides such as barium hexafluorosilicate, cryolite, sodium fluoride, sodium hexafluorosilicate and sulfluramid; formamidine insecticides such as amitraz, chlordimeform, formetanate and formparanate; fumigant insecticides such as acrylonitrile, carbon disulfide, carbon tetrachloride, chloroform, chloropicrin, para-dichlorobenzene, 1,2-dichloropropane, ethyl formate, ethylene dibromide, ethylene dichloride, ethylene oxide, hydrogen cyanide, iodomethane, methyl bromide, methylchloroform, methylene chloride, naphthalene, phosphine, sulfuryl fluoride and tetrachloroethane; inorganic insecticides such as borax, calcium polysulfide, copper oleate, mercurous chloride, potassium thiocyanate and sodium thiocyanate; chitin synthesis inhibitors such as bistrifluoron, buprofezin, chlorfluazuron, cyromazine, diflubenzuron, flucycloxuron, flufenoxuron, hexaflumuron, lufenuron, novaluron, noviflumuron, penfluoron, teflubenzuron and triflumuron; juvenile hormone mimics such as epofenonane, fenoxycarb, hydroprene, kinoprene, methoprene, pyriproxyfen and triprene; juvenile hormones such as juvenile hormone I, juvenile hormone II and juvenile hormone III; moulting hormone agonists such as chromafenozide, halofenozide, methoxyfenozide and tebufenozide; moulting hormones such as α-ecdysone and ecdysterone; moulting inhibitors such as diofenolan; precocenes such as precocene I, precocene II and precocene III; unclassified insect growth regulators such as dicyclanil; nereistoxin analogue insecticides such as bensultap, cartap, thiocyclam and thiosultap; nicotinoid insecticides such as flonicamid; nitroguanidine insecticides such as clothianidin, dinotefuran, imidacloprid and thiamethoxam; nitromethylene insecticides such as nitenpyram and nithiazine; pyridylmethylamine insecticides such as acetamiprid, imidacloprid, nitenpyram and thiacloprid; organochlorine insecticides such as bromo-DDT, camphechlor, DDT, pp'-DDT, ethyl-DDD, HCH, gamma-HCH, lindane, methoxychlor, pentachlorophenol and TDE; cyclodiene insecticides such as aldrin, bromocyclen, chlorbicyclen, chlordane, chlordecone, dieldrin, dilor, endosulfan, endrin, HEOD, heptachlor, HHDN, isobenzan, isodrin, kelevan and mirex; organophosphate insecticides such as bromfenvinfos, chlorfenvinphos, crotoxyphos, dichlorvos, dicrotophos, dimethylvinphos, fospirate, heptenophos, methocrotophos, mevinphos, monocrotophos, naled, naftalofos, phosphamidon, propaphos, TEPP and tetrachlorvinphos; organothiophosphate insecticides such as dioxabenzofos, fosmethilan and phenthoate; aliphatic organothiophosphate insecticides such as acethion, amiton, cadusafos, chlorethoxyfos, chlormephos, demephion, demephion-O, demephion-S, demeton, demeton-O, demeton-S, demeton-methyl, demeton-O-methyl, demeton-S-methyl, demeton-S-methylsulphon, disulfoton, ethion, ethoprophos, IPSP, isothioate, malathion, methacrifos, oxydemeton-methyl, oxydeprofos, oxydisulfoton, phorate, sulfotep, terbufos and thiometon; aliphatic amide organothiophosphate insecticides such as amidithion, cyanthoate, dimethoate, ethoatemethyl, formothion, mecarbam, omethoate, prothoate, sophamide and vamidothion; oxime organothiophosphate insecticides such as chlorphoxim, phoxim and phoxim-methyl; heterocyclic organothiophosphate insecticides such as azamethiphos, coumaphos, coumithoate, dioxathion, endothion, menazon, morphothion, phosalone, pyraclofos, pyridaphenthion and quinothion; benzothiopyran organothiophosphate insecticides such as dithicrofos and thicrofos; benzotriazine organothiophosphate insecticides such as azinphos-ethyl and azinphos-methyl; isoindole organothiophosphate insecticides such as dialifos and phosmet; isoxazole organothiophosphate insecticides such as isoxathion and zolaprofos; pyrazolopyrimidine organothiophosphate insecticides such as chlorprazophos and pyrazophos; pyridine organothiophosphate insecticides such as chlorpyrifos and chlorpyrifos-methyl; pyrimidine organothiophosphate insecticides such as butathiofos, diazinon, etrimfos, lirimfos, pirimiphos-ethyl, pirimiphos-methyl, primidophos, pyrimitate and tebupirimfos; quinoxaline organothiophosphate insecticides such as quinalphos and quinalphos-methyl; thiadiazole organothiophosphate insecticides such as athidathion, lythidathion, methidathion and prothidathion; triazole organothiophosphate insecticides such as isazofos and triazophos; phenyl organothiophosphate insecticides such as azothoate, bromophos, bromophos-ethyl, carbophenothion, chlorthiophos, cyanophos, cythioate, dicapthon, dichlofenthion, etaphos, famphur, fenchlorphos, fenitrothion, fensulfothion, fenthion, fenthion-ethyl, heterophos, jodfenphos, mesulfenfos, parathion, parathion-methyl, phenkapton, phosnichlor, profenofos, prothiofos, sulprofos, temephos, trichlormetaphos-3 and trifenofos; phosphonate insecticides such as butonate and trichlorfon; phosphonothioate insecticides such as imicyafos and mecarphon; phenyl ethylphosphonothioate insecticides such as fonofos and trichloronat; phenyl phenylphosphonothioate insecticides such as cyanofenphos, EPN and leptophos; phosphoramidate insecticides such as crufomate, fenamiphos, fosthietan, mephosfolan, phosfolan and pirimetaphos; phosphoramidothioate insecticides such as acephate, isocarbophos, isofenphos, methamidophos and propetamphos; phosphorodiamide insecticides such as dimefox, mazidox, mipafox and schradan; oxadiazine insecticides such as indoxacarb; phthalimide insecticides such as dialifos, phosmet and tetramethrin; pyrazole insecticides such as acetoprole, ethiprole, fipronil, pyrafluprole, pyriprole, tebufenpyrad, tolfenpyrad and vaniliprole; pyrethroid ester insecticides such as acrinathrin, allethrin, bioallethrin, barthrin, bifenthrin, bioethanomethrin, cyclethrin, cyclopropthrin, cyfluthrin, beta-cyfluthrin, cyhalothrin, gamma-cyhalothrin, lambda-cyhalothrin, cypermethrin, alpha-cypermethrin, beta-cypermethrin, theta-cypermethrin, zeta-cypermethrin, cyphenothrin, deltamethrin, dimefluthrin, dimethrin, empenthrin, fenfluthrin, fenpirithrin, fenpropathrin, fenvalerate, esfenvalerate, flucythrinate, fluvalinate, tau-fluvalinate, furethrin, imiprothrin, metofluthrin, permethrin, biopermethrin, transpermethrin, phenothrin, prallethrin, profluthrin, pyresmethrin, resmethrin, bioresmethrin, cismethrin, tefluthrin, terallethrin, tetramethrin, tralomethrin and transfluthrin; pyrethroid ether insecticides such as etofenprox, flufenprox, halfenprox, protrifenbute and silafluofen; pyrimidinamine insecticides such as flufenerim and pyrimidifen; pyrrole insecticides such as chlorfenapyr; ryanodine receptor insecticides such as flubendiamide, chlorantraniliprole (rynaxypyr) and cyantranilipole; tetronic acid insecticides such as spirodiclofen, spiromesifen and spirotetramat; thiourea insecticides such as diafenthiuron; urea insecticides such as flucofuron and sulcofuron; sulfoximine insecticides such as sulfoxaflor and unclassified insecticides such as closantel, crotamiton, EXD, fenazaflor, fenazaquin, fenoxacrim, fenpyroximate, flubendiamide, hydramethylnon, isoprothiolane, malonoben, metaflumizone, metoxadiazone, nifluridide, pyridaben, pyridalyl, pyrifluquinazon, rafoxanide, triarathene and triazamate. The present disclosure contemplates selecting insecticides from this list with water solubilities of about 1000 ppm or less and formulating them as mesoparticles with built-in or tank-mixed adjuvant. Preferable insecticides are those with water solubilities of about 100 ppm or less. More preferable insecticides are those with water solubilities of 10 ppm or less. Insecticides can be chosen based on water solubilities published in compendia such as The Pesticide Manual Fourteenth Edition, (ISBN 1-901396-14-2), which is incorporated herein by reference in its entirety. Future editions of The Pesticide Manual will also be useful for selecting insecticides for incorporation into mesoparticles.

Many classes and types of fungicides are useful in agriculture. Examples include ametoctradin, amisulbrom 2-(thiocyanatomethylthio)-benzothiazole, 2-phenylphenol, 8-hydroxyquinoline sulfate, antimycin, azaconazole, azoxystrobin, benalaxyl, benomyl, benthiavalicarb-isopropyl, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, BYF 1047, calcium polysulfide, captafol, captan, carbendazim, carboxin, carpropamid, carvone, chloroneb, chlorothalonil, chlozolinate, copper hydroxide, copper octanoate, copper oxychloride, copper sulfate, copper sulfate (tribasic), cuprous oxide, cyazofamid, cyflufenamid, cymoxanil, cyproconazole, cyprodinil, coumarin, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, meptyl dinocap, diphenylamine, dithianon, dodemorph, dodemorph acetate, dodine, dodine free base, edifenphos, enestrobin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutolanil, flutriafol, fluxapyrad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), ipconazole, iprobenfos, iprodione, iprovalicarb, isoprothiolane, isopyrazam, isotianil, kasugamycin, kasugamycin hydrochloride hydrate, kresoxim-methyl, mancopper, mancozeb, mandipropamid, maneb, mepanipyrim, mepronil, meptyldinocap, mercuric chloride, mercuric oxide, mercurous chloride, metalaxyl, mefenoxam, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, penflufen, pefurazoate, penconazole, pencycuron, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyraxostrobin, pyrazophos, pyribencarb, pyributicarb, pyrifenox, pyrimethanil, pyriofenone, pyrometostrobin, pyroquilon, quinoclamine, quinoxyfen, quintozene, Reynoutria sachalinensis extract, sedaxane, silthiofam, simeconazole, sodium 2-phenylphenoxide, sodium bicarbonate, sodium pentachlorophenoxide, spiroxamine, sulfur, SYP-Z071, SYP-048, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazolopyrimidine, triazoxide, tricyclazole, tridemorph, trifloxystrobin, triflumizole, triforine, triticonazole, validamycin, valiphenal, valifenate, vinclozolin, zineb, ziram, zoxamide, (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme: ampropylfos, anilazine, azithiram, barium polysulfide, Bayer 32394, benodanil, benquinox, bentaluron, benzamacril; benzamacril-isobutyl, benzamorf, binapacryl, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, UK-2A, derivatives of UK-2A such as, for example, (3S,6S,7R,8R)-8-benzyl-3-(3-(isobutyryloxymethoxy)-4-methoxypicolinamido)-6-methyl-4,9-dioxo-1,5-dioxonan-7-yl isobutyrate which has a CAS Registry Number of 328255-92-1 and will be referred to herein as 328255-92-1, urbacid, XRD-563, zarilamid, IK-1140, and propargyl amides. The present disclosure contemplates selecting fungicides from this list with water solubilities of about 1000 ppm or less and formulating them as mesoparticles with built-in or tank-mixed adjuvant. Preferable fungicides are those with water solubilities of about 100 ppm or less. More preferable fungicides are those with water solubilities of 10 ppm or less. Fungicides can be chosen based on water solubilities published in compendia such as The Pesticide Manual Fourteenth Edition, ISBN 1-901396-14-2, which is incorporated herein by reference in its entirety. Future editions of The Pesticide Manual will also be useful for selecting fungicides for incorporation into mesoparticles.

Many classes and types of herbicides are useful in agriculture. Examples include amide herbicides such as allidochlor, beflubutamid, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, isoxaben, napropamide, naptalam, pethoxamid, propyzamide, quinonamid and tebutam; anilide herbicides such as chloranocryl, cisanilide, clomeprop, cypromid, diflufenican, etobenzanid, fenasulam, flufenacet, flufenican, mefenacet, mefluidide, metamifop, monalide, naproanilide, pentanochlor, picolinafen and propanil; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, dicamba, 2,3,6-TBA and tricamba; pyrimidinyloxybenzoic acid herbicides such as bispyribac and pyriminobac; pyrimidinylthiobenzoic acid herbicides such as pyrithiobac; phthalic acid herbicides such as chlorthal; picolinic acid herbicides such as aminopyralid, clopyralid and picloram; quinolinecarboxylic acid herbicides such as quinclorac and quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, sulcotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim, tepraloxydim and tralkoxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazamethabenz, imazamox, imazapic, imazapyr, imazaquin and imazethapyr; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, bromoxynil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, dichlorprop, dichlorprop-P, 3,4-DP, fenoprop, mecoprop and mecoprop-P; aryloxyphenoxypropionic herbicides such as chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrasulfotole, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, norflurazon, oxapyrazon and pydanon; pyridine herbicides such as aminopyralid, cliodinate, clopyralid, dithiopyr, fluoroxypyr, fluoroxypyr-meptyl, haloxydine, picloram, picolinafen, pyriclor, thiazopyr and triclopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, prosulfocarb, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin, metamitron and metribuzin; triazole herbicides such as amitrole, cafenstrole, epronaz and flupoxam; triazolone herbicides such as amicarbazone, bencarbazone, carfentrazone, flucarbazone, propoxycarbazone, sulfentrazone and thiencarbazone-methyl; triazolopyrimidine herbicides such as cloransulam, diclosulam, florasulam, flumetsulam, metosulam, penoxsulam and pyroxsulam; uracil herbicides such as butafenacil, bromacil, flupropacil, isocil, lenacil and terbacil; 3-phenyluracils; urea herbicides such as benzthiazuron, cumyluron, cycluron, dichloralurea, diflufenzopyr, isonoruron, isouron, methabenzthiazuron, monisouron and noruron; phenylurea herbicides such as anisuron, buturon, chlorbromuron, chloreturon, chlorotoluron, chloroxuron, daimuron, difenoxuron, dimefuron, diuron, fenuron, fluometuron, fluothiuron, isoproturon, linuron, methiuron, methyldymron, metobenzuron, metobromuron, metoxuron, monolinuron, monuron, neburon, parafluoron, phenobenzuron, siduron, tetrafluoron and thidiazuron; pyrimidinylsulfonylurea herbicides such as amidosulfuron, azimsulfuron, bensulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, nicosulfuron, orthosulfamuron, oxasulfuron, primisulfuron, pyrazosulfuron, rimsulfuron, sulfometuron, sulfosulfuron and trifloxysulfuron; triazinylsulfonylurea herbicides such as chlorsulfuron, cinosulfuron, ethametsulfuron, iodosulfuron, metsulfuron, prosulfuron, thifensulfuron, triasulfuron, tribenuron, triflusulfuron and tritosulfuron; thiadiazolylurea herbicides such as buthiuronk, ethidimuron, tebuthiuron, thiazafluoron and thidiazuron; and unclassified herbicides such as acrolein, allyl alcohol, azafenidin, benazolin, bentazone, benzobicyclon, buthidazole, calcium cyanamide, cambendichlor, chlorfenac, chlorfenprop, chlorflurazole, chlorflurenol, cinmethylin, clomazone, CPMF, cresol, ortho-dichlorobenzene, dimepiperate, endothal, fluoromidine, fluridone, fluorochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, pinoxaden, prosulfalin, pyribenzoxim, pyriftalid, quinoclamine, rhodethanil, sulglycapin, thidiazimin, tridiphane, trimeturon, tripropindan and tritac. The present disclosure contemplates selecting herbicides from this list with water solubilities of about 1000 ppm or less and formulating them as mesoparticles with built-in or tank-mixed adjuvant. Preferable herbicides are those with water solubilities of about 100 ppm or less. More preferable herbicides are those with water solubilities of 10 ppm or less. Herbicides can be chosen based on water solubilities published in compendia such as The Pesticide Manual Fourteenth Edition, ISBN 1-901396-14-2, which is incorporated herein by reference in its entirety. Future editions of The Pesticide Manual will also be useful for selecting herbicides for incorporation into mesoparticles.

Many classes and types of modifiers of plant physiology or structure are useful in agriculture. Examples include ancymidol, aminoethoxyvinylglycine, 6-benzylaminopurine, carvone, chlorflurenol-methyl, chlormequat chloride, cloxyfonac, 4-CPA, cyclanilide, cytokinins, daminozide, dikegulac, ethephon, flurenol, flurprimidol, forchlorfenuron, gibberellic acids, gibberellins, inabenfide, indol-3-ylacetic acid, 4-indol-3-ylbutyric acid, maleic hydrazide, mepiquat chloride, 1-methylcyclopropene, 2-(1-napthyl)acetamide, 1-napthylacetic acid, 2-napthyloxyacetic acid, nitrophenolates, paclobutrazol, N-phenylphthalamic acid, prohexadione-calcium, n-propyl dihydrojasmonate, thidiazuron, tribufos, trinexepac-ethyl, and uniconazole. The present disclosure contemplates selecting modifiers from this list with water solubilities of about 1000 ppm or less and formulating them as mesoparticles with built-in or tank-mixed adjuvant. Preferable modifiers are those with water solubilities of about 100 ppm or less. More preferable modifiers are those with water solubilities of 10 ppm or less. Modifiers can be chosen based on water solubilities published in compendia such as The Pesticide Manual Fourteenth Edition, ISBN 1-901396-14-2, which is incorporated herein by reference in its entirety. Future editions of The Pesticide Manual will also be useful for selecting modifiers of plant physiology or structure for incorporation into mesoparticles.

Mesoparticle formulations of herbicides in accordance with various embodiments can be used in combination with a wide variety of herbicide safeners, including safeners such as benoxacor, benthiocarb, brassinolide, cloquintocet (mexyl), cyometrinil, cyprosulfamide, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenylsulfonylbenzoic acid amides. The level of active ingredient in the mesoparticle used to prepare these formulations can range from about 0.001 wt. % to about to 99 wt. %. It is contemplated that mesoparticle formulations of herbicides can be combined with built-in or tank-mixed adjuvants and herbicide safeners. It is further contemplated that the herbicide safeners themselves can be formulated as mesoparticles, as conventional-sized particles or even solublized directly into the formulation containing herbicide mesoparticles and built-in adjuvants.

It is contemplated that mesoparticles and adjuvants of the present disclosure can be used with many conventional formulation ingredients such as aqueous or non-aqueous solvent media or diluents in which the mesoparticles are suspended or slurried at a concentration of the agricultural active ingredient, with respect to the formulation, from about 0.1% to about 95% and, more commonly in the range of about 5 to about 50%. The adjuvant may be included in these conventional formulations containing mesoparticles at a concentration of, with respect to the formulation, from about 0.1% to about 90% and, more commonly in the range of about 5 to about 50%. Conventional inactive or inert ingredients such as dispersants, thickening agents, stickers, film-forming agents, buffers, emulsifiers, anti-freezing agents, dyes, stabilizers, solid carriers and the like may also be incorporated into these formulations containing mesoparticles and adjuvants.

It is contemplated that formulations of agricultural AIs contained in mesoparticles combined with built-in or tank-mixed adjuvants, especially penetrant adjuvants, can be utilized to control insects, mites, plant diseases or weeds by providing and applying an agriculturally effective amount of the mesoparticle formulation to at least one of the following: the plant, plant foliage, blossoms, stems, fruits, the area adjacent to the plant, soil, seeds, germinating seeds, roots, liquid and solid growth media, and hydroponic growth solutions. The mesoparticle formulation combined with built-in or tank-mixed adjuvants can be diluted in a suitable agricultural diluent, such as water, and applied by any conventional method, including but not limited to: 1) application as a foliar spray, preferably in sufficient volume to wet the foliage, 2) application as a drench to soil, 3) application to seeds, 4) application by drip irrigation, and 5) application by injection into soil or hydroponic growth media. It is further envisioned that mesoparticle formulations can be applied in mixture with conventional formulations of agricultural AIs, plant nutrients and growth regulators. Conventional formulations of agricultural AI's include solutions such as oil in water or water in oil dispersions, emulsifiable concentrates, solutions of AIs in water, sprayable concentrates of AIs as suspended particulates with a volume average diameter of about 1 micron or larger, AIs in the form of wettable powders with a volume average diameter of about 1 micron or larger and AIs in the form of granules with a volume average diameter of about 10 microns or larger.

EXAMPLES

Particle Size Measurements

The particle size can be determined in particular by the known method of quasi-elastic light scattering. One apparatus that can be used for this determination is the Brookhaven 90Plus Nanoparticle Size Analyzer. This apparatus provides a measure of the average diameter by photon correlation spectroscopy (or PCS). In addition, the Malvern MasterSizer 2000 may also be used for particle size measurements. Alternatively, particle size may be measured by other known techniques including centrifugation or electron microscopy.

Synthesis of Mesoparticles

Preparation of Stock Solutions of Amino Acids Used to Synthesize Mesocapsules.

Before the initiation of the various reaction runs used to synthesize the exemplary mesocapsules disclosed herein, stock solutions of glycine and lysine were prepared in the proportions listed in FIG. 1.

General Methods Used to Prepare the Polyurea Mesocapsules Disclosed Herein.

A typical method used to synthesize a representative polyurea mesoparticle formulation is set forth below using the ingredients and quantities listed in FIG. 2. Briefly, fenbuconazole, benzyl acetate, hexadecane, and PAPI™ 27 polymeric MDI (The Dow Chemical Co.) were added to a 60 ml jar and mixed until uniform. Surfactant, water, and glycine solutions were added to the jar and mixed with a hand-held Biohomogenizer mixer for about 10 seconds to create a pre-emulsion. The jar was placed in an ice bath and the pre-emulsion was sonicated for 5 minutes using a Branson 184V Ultrasonicator at 40% power to create the final emulsion which was converted into the polyurea mesocapsules by addition of the cross-linker. The particle volume-average diameter of mesocapsules in each sample was measured using a Brookhaven 90Plus Nanoparticle Size Analyzer. The mesocapsule formulations listed in FIG. 2 were made using this method. As indicated in FIG. 2, the compositions of the reaction mixtures were varied to create the formulations disclosed herein. The formulations referenced in FIG. 6 were tested on plants to determine their curative and preventative plant disease control properties.

The following procedure was utilized with the ingredients and quantities listed in FIG. 3 to make mesocapsule suspensions of epoxiconazole (sample 15), fluoroxypyr-meptyl (sample 16B) and 328255-92-1 (sample 14). An oil phase and aqueous phase were prepared separately. The active ingredient 328255-92-1 was dissolved in the solvent mixture to make 77% of the oil phase, followed by the addition of 3% of the hydrophobe and 20% of the isocyanate ($1^{st}$ monomer) to provide the complete oil phase. To the aqueous phase were added Proxel™ GXL (Arch UK Biocides, Ltd.; 0.1% of total formulation) and sodium lauryl sulfate (3% of oil phase). The aqueous phase was combined with the oil phase and the mixture was magnetically stirred for 2 minutes to make a pre-emulsion, which was subsequently sonicated for 4-5 minutes using a Vibra Cell™ (Sonics & Materials, Inc.) at 750 W and 24-25% amplitude in an ice/water bath to make a stable oil-in-water emulsion at the meso scale. Upon stirring, polyamine ($2^{nd}$ monomer) was added to react with the isocyanate to form the polyurea shell. The formulation samples 14, 15 and 16B referenced in FIG. 6 were tested on plants to determine their pest control properties.

General Method Used to Prepare the Latex Meso-Matrix Particles Disclosed Herein.

A typical method used to synthesize a representative latex meso-matrix particle formulation is set forth below. The aqueous and oil the phases were prepared separately. To prepare the aqueous phase, add the desired amount of surfactant to DI water in an 8-oz glass jar. To prepare the oil phase, measure the fenbuconazole, initiator, monomer, co-monomer, dye monomer, and ultrahydrophobe. After both solutions are transparent, add the oil phase into the aqueous phase with magnetic stirring. This mixture was pre-emulsified in an ice-water bath with magnetic stirring for 30 minutes. The above emulsion was sonicated (450 watts, 100 mL, 6-8 minutes) in an ice-water bath to produce a stable oil-in-water miniemulsion. 50 mL of the resulting miniemulsion was added to a 250 mL round bottom glass reactor flask, and the flask degassed 3-4 times under vacuum/$N_2$ purge. The miniemulsion was polymerized at 75° C. under nitrogen for 1-2 hours. FIG. 4 shows the specific amounts of each reagent used. The polymerized formulations were used as is, or diluted to achieve the desired level of active ingredient and were tested on plants to determine their curative and preventative plant disease control properties.

General Method Used to Prepare the Meso-Homogeneous Particles Disclosed Herein.

A typical method used to prepare a representative meso-homogeneous particle formulation is set forth below. Using the ingredients and amounts shown in FIG. 5, an aqueous phase was prepared containing 328255-92-1, Pluronic™ P105 (BASF Corporation), Morwet™ D425 (AkzoNobel), Dow Corning™ Antifoam B (Dow Corning Corporation) and water. The aqueous phase was placed in a plastic bottle with 50 grams of ⅛ inch diameter stainless steel milling balls and sealed. The sample was shaken on a horizontal reciprocal shaker at high frequency for 24-72 hours depending on the nature of the AI crystals. The particle size of the AI was monitored periodically with a Malvern MasterSizer 2000 until it reached a target volume average diameter of less than about 300 nm. The aqueous suspension of the meso-homogeneous particles was separated and transferred from the milling beads into a clean vial using a needle tip pipet and was used in efficacy testing as is, or diluted to achieve the desired level of active ingredient.

Biological Evaluation of Compositions of Mesoparticles

Referring now to FIG. 6, the table includes a listing of the formulations that were tested. The formulations of mesoparticles of fenbuconazole listed in FIG. 6 were tested to measure their curative and protectant effects on wheat leaf blotch disease, which is caused by the fungus *Septoria tritici*. Latex meso-matrix particle and polyurea mesocapsule particle formulations of fenbuconazole were tested for curative and protectant effects on leaf blotch disease of wheat on separate sets of wheat (cultivar Yuma) plants Each formulation was diluted in water and tested at the rates of 125, 41.4, 13.8, 4.6 and 1.4 g active substance/Ha. Each of the four meso-formulations was tested with and without Uptake Oil™ (Dow Agro-Sciences, LLC) at the rate of 0.5% v/v in the final spray solution. Uptake Oil is a penetrant adjuvant comprised of 582 g/L paraffinic oil, 7.5 g/L oleic acid, 145 g/L Polyglycol 26-2 surfactant (The Dow Chemical Company), 95 g/L Teric™ 12-A3 (Huntsman Corporation) emulsifier and 42.5 g/L Aromatic 150. Referring to FIG. 6, a mesocapsule formulation of 328255-92-1 was tested with and without Uptake™ or Trycol 5941; a mesocapule formulation of epoxiconazole was tested with and without Uptake™; and a meso-homogeneous formulation of epoxiconazole was tested with and without Emery Emgard. Each formulation was diluted in water and tested at the rates of 62.5, 20.8, 6.9, 2.3 and 0.8 g active substance/Ha. Experimental units for these tests consisted of 8 to 10 wheat plants grown in 5 cm by 5 cm pots of growth media comprised of half MetroMix and half clay loam soil. Each treatment was replicated four times and treatments were randomized after chemicals were applied.

Plants for the curative test were inoculated in the 2-leaf stage of growth two or three days before formulations were applied, depending on the test. For the protectant test, formulations were applied in the two leaf stage of growth and plants were inoculated three or four days later, depending on the test. Treatments were applied using a Gen III Research Sprayer (DeVries Mfg., Hollandale Minn.) tracksprayer calibrated to deliver 100 L/Ha and equipped with a Spraying Systems 8002E TeeJet spray nozzle.

Inoculum of the foliar pathogen, Septoria tritici, was prepared by harvesting conidia from freshly erumpent and mature pycnidia. An aqueous suspension of conidia was made by counting several samples in a hemocytometer and then adjusting the suspension to 1,000,000 conidia/ml. Plants were inoculated by applying a fine mist with a low pressure compressed air sprayer at a volume of approximately 200 ml inoculum per 80 pots of wheat. After inoculation, plants were incubated in a dark dew room (22 C) at 99-100% relative humidity for 24 hours, then moved to a lighted dew room (20 C) at 99-100% relative humidity for an additional 48 hrs and then placed in a greenhouse set at 20 C and a 14-hr photoperiod for the remainder of the test. Plant growth was maintained through regular application of dilute liquid fertilizer solution.

Wheat seedlings were rated for disease approximately 21 days after the inoculation. Percent disease was assessed by making a visual estimate of the percent of the leaf showing disease symptoms. Plants that were first inoculated and then treated with chemical two days later provided indications of curative effects. Plants that were first treated and then inoculated four days later provide indications of protectant effects. The level of disease on untreated check plants in the curative test was 82%. The level of disease on untreated check plants in the protectant test was 95%.

Percent disease was converted to percent disease control using the following formula:
(Average % disease in untreated check−average % disease in treatment)/(Average % disease in untreated check)×100%. The percent disease control in each series of meso-formulations applied with adjuvant was compared to the actual and expected levels of control for the same series applied without adjuvant using the Colby Equation.

Referring now to FIGS. 7 and 8, the results of the various tests are as follows. In the curative and protectant tests (FIG. 7), the addition of Uptake Oil™ resulted in an enhancement of the curative and protectant effectiveness of all meso-formulations of fenbuconazole on leaf blotch. FIG. 8 shows a comparison of the enhancement ratios for the 4 meso-formulations to the enhancement ratio for fenbuconazole 75% WP. The enhancement ratio is a calculation made by dividing the factorial mean disease control across rates without oil by the factorial mean across rates with Uptake Oil™. The calculations show that, whether indicated by curative data or by protectant data, the level of enhancement experienced by meso-sized formulations is considerably greater than the enhancement of 75 WP.

Various meso-particle formulations of fungicides were tested for protectant or curative effects on brown rust of wheat. A polyurea meso-capsule formulation of 328255-92-1 (Sample 14) and a meso-homogeneous particle formulation of 328255-92-1 (Sample 68B) were tested for protectant effects on brown rust of wheat which is caused by the fungus, *Puccinia recondita* f. sp. *Tritici*. The test was conducted on wheat plants (cultivar Yuma). Each formulation was diluted in water and tested at the rates of 62.5, 20.8, and 6.9, g active substance/Ha. The meso-formulation was tested with and without Uptake Oil™ at the rate of 0.5% v/v in the final spray solution. Each experimental unit consisted of 8 to 10 wheat plants grown in 5 cm by 5 cm pots of growth media comprised of half MetroMix and half clay loam soil. Each treatment was replicated four times and treatments were randomized after chemicals were applied.

Plants for the curative test were inoculated in the 2-leaf stage of growth two days before formulations were applied. For the protectant test, formulations were applied in the two leaf stage of growth and plants inoculated four days later with the fungus that causes brown rust. Referring now to FIG. 6, various mesoparticle formulations were tested for curative effects on brown rust of wheat. A mesocapsule formulation of 328255-92-1 was tested with and without Uptake™ or Trycol®5941; a mesocapule formulation of epoxiconazole was tested with and without Uptake™; and a meso-homogeneous formulation of epoxiconazole was tested with and without Emery Emgard. Each formulation was diluted in water and tested at the rates of 62.5, 20.8, 6.9, 2.3 and 0.8 g active substance/Ha Treatments were applied using a Gen III Research Sprayer (DeVries Mfg., Hollandale Minn.) tracksprayer equipped with a Spraying Systems 8002E TeeJet spray nozzle and calibrated to deliver 100 L/Ha.

Inoculum of the foliar pathogen, *Puccinia recondita* f. sp. *tritici*, was prepared by harvesting urediospores from freshly erumpent and mature pustules. The final aqueous suspension of urediospores was made using the following ratios 0.1 g of urediospores, added to three drops of Tween 20, and then mixed as a paste. To the paste was added 100 ml of distilled water. The suspension yielded approximately 1,000,000 uredia/ml. Plants were inoculated by applying a fine mist with a low pressure compressed air sprayer at a volume of approximately 300 ml per 80 pots of wheat. After inoculation, plants were incubated in a dark dew room (22° C.) at 99-100% relative humidity for 24 hours and then moved to a greenhouse set at 24° C. and a 14-hr photoperiod for the remainder of the test. Plant growth was maintained through regular application of dilute liquid fertilizer solution.

The wheat seedlings were rated for disease approximately 7-8 days after the inoculation. Percent disease was assessed by making a visual estimate of the percent disease on the primary leaf.

Referring now to FIG. 9, the results of the test indicate that the addition of Uptake Oil™ (Dow AgroSciences, LLC) resulted in an enhancement of the protectant effectiveness of the meso-capsule formulation of 328255-92-1 on brown rust.

Referring now to FIG. 10, the results of the test indicate that the addition of Uptake Oil™ (Dow AgroSciences, LLC) resulted in an enhancement of the protectant effectiveness of the meso-homogeneous formulation of 328255-92-1 on brown rust.

Referring now to FIG. 11, the results of the test indicate that the addition of Uptake™ (Dow AgroSciences, LLC) or Trycol®5941 (Cognis Corporation) resulted in an enhancement of the curative effectiveness of the meso-capsule formulation of 328255-92-1 on brown rust. Further, the results of the test indicate that the addition of Uptake™ (Dow AgroSciences, LLC) or Trycol®5941 resulted in an enhancement of the curative effectiveness of the meso-capsule formulation of 328255-92-1 on brown rust. Further, the results of the test indicate that the addition of Uptake™ (Dow AgroSciences, LLC) resulted in an enhancement of the curative effectiveness of the meso-capsule formulation of epoxiconazole on brown rust and that the addition of Emery Emgard (an 85:15 wt % blend of Agnique ME 181-u (formerly known as Emery 2301; Cognis Corporation) and Emgard 2033 (Cognis Corporation)) resulted in an enhancement of the curative effectiveness of the meso-homogeneous formulation of epoxiconazole on brown rust.

Referring now to FIG. 12, the results of the test indicate that the addition of Uptake™ (Dow AgroSciences, LLC) or Trycol®5941 (Cognis Corporation) resulted in an enhancement of the protectant effectiveness of the meso-capsule formulation of 328255-92-1 on leaf blotch. Further, the results of the test indicate that the addition of Uptake™ (Dow AgroSciences, LLC) resulted in an enhancement of the protectant effectiveness of the meso-capsule formulation of epoxiconazole on leaf blotch.

Referring now to FIG. 13, the results of the test indicate that the addition of Uptake™ (Dow AgroSciences, LLC) or Trycol®5941 resulted in an enhancement of the curative effectiveness of the meso-capsule formulation of 328255-92-1 on leaf blotch. Further, the results of the test indicate that the addition of Uptake™ (Dow AgroSciences, LLC) resulted in an enhancement of the curative effectiveness of the meso-capsule formulation of epoxiconazole on leaf blotch and that the addition of Emery Emgard (an 85:15 wt % blend of Agnique ME 181-u (formerly known as Emery 2301; Cognis Corporation) and Emgard 2033 (Cognis Corporation)) resulted in an enhancement of the curative effectiveness of the meso-homogeneous formulation of epoxiconazole on leaf blotch.

Referring now to FIG. 6 the table includes a listing of the formulations that were tested containing the herbicidal active ingredients atrazine, fluoroxypyr-meptyl and pyroxsulam. The polyurea mesocapsule and meso-homogeneous particle formulations made in accordance with the various embodiments disclosed herein were compared with and without the addition of 0.25% v/v Agral 90 (Norac Concepts Inc.) or 2.0% v/v crop oil concentrate (COC, Agri-dex; Helena Chemical Co.). The polyurea mesocapsule formulation of fluoroxypyr-meptyl and the meso-homogeneous particle formulations of atrazine and pyroxsulam listed in FIG. 6 were tested to measure their post-emergence herbicidal effects on various dicot and monocot weed species utilizing the methods described herein.

A peat based potting soil, Metro-mix 360, was used as the soil media for this test. Metro-mix is a growing medium consisting of 35 to 45% specially processed coconut coir pith, 10 to 20% horticultural grade vermiculite, 15 to 25% processed ash bark, 20 to 30% choice Canadian Sphagnum Peat Moss and proprietary nutrients and other ingredients. Several seeds of each species were planted in 10 cm square pots and top watered twice daily. Wild buckwheat, *Polygonum convolvulus* (POLCO), Velvetleaf, *Abutilon theophrasti* (ABUTH), Wild oat, *Avena fatua* (AVEFA), Blackgrass, *Alopecurus myosuroides* (ALOMY), Redroot pigweed, *Amaranthus retroflexus* (AMARE), Wild poinsettia, *Euphorbia heterophylla* (EPHHL), Common Chickweed, *Stellaria media* (STEME), Field Violet, *Viola arvensis* (VIOAR) and Common Lambsquarters, *Chenopodium album* (CHEAL) were propagated in the greenhouse at a constant temperature of 26 to 28° C. and 50 to 60% relative humidity. Natural light was supplemented with 1000-watt metal halide overhead lamps with an average illumination of 500 uE m-2 s-1 photosynthetic active radiation (PAR). The photoperiod was 16 hr. Plant material was top-watered prior to treatment and sub-irrigated after treatment.

The meso-formulation of atrazine was applied at 560 g active ingredient/Ha. The meso-formulation of fluoroxypyr-meptyl was tested at rates of 100, 50, 25 and 12.5 g acid equivalent/Ha and the meso-formulation of pyroxsulam was tested at 1.17, 2.34, and 4.7 g active ingredient/Ha. All three of the formulations were diluted in tap water and applied alone, with Agral 90 (Norac Concepts Inc.) at 0.25% v/v or with crop oil concentrate (COC, Agri-dex; Helena Chemical Co.) at 2% v/v. Treatments were applied with a tracksprayer manufactured by Allen Machine Works. The sprayer utilized an 8002E spray nozzle, spray pressure of 262 kPa pressure and speed of 1.8 mph to deliver 187 L/Ha. The nozzle height was 46 cm above the plant canopy. The growth stage of the various weed species ranged from 2 to 4 leaf. Treatments were replicated 1, 2 or 3 times depending on the availability of plant material. Plants were returned to the greenhouse after treatment and sub-watered throughout the duration of the experiment. Plant material was fertilized twice weekly with Hoagland's fertilizer solution. Visual assessments of percent control were made on a scale of 0 to 100% as compared to the untreated control plants (where 0 is equal to no control and 100 is equal to complete control).

Referring now to FIG. 14, the results of the post-emergence herbicide test indicate that use of the meso-homogeneous particle formulation of atrazine with either Agral 90 at 0.25% v/v or with crop oil concentrate (COC, Agri-dex; Helena Chemical Co.) at 2% v/v resulted in generally higher levels of control when compared to use of the meso-homogeneous particle formulation of atrazine alone. Use of the mesocapsule formulation of fluoroxypyr-meptyl with either Agral 90 (Norac Concepts Inc.) at 0.25% v/v or with crop oil concentrate (COC, Agri-dex; Helena Chemical Co.) at 2% v/v resulted in generally higher levels of control when compared to the mesocapsule formulation of fluoroxypyr-meptyl alone. Use of the meso-homogeneous particle formulation of pyroxsulam with either Agral 90 at 0.25% v/v or with crop oil concentrate (COC, Agri-dex; Helena Chemical Co.) at 2% v/v resulted in generally higher levels of control when compared to use of the meso-homogeneous particle formulation of pyroxsulam alone.

We claim:

1. A composition comprising:
   a) a mesoparticle selected from the group consisting of a mesocapsule, a meso-matrix particle, and a meso-homogenous particle, the mesoparticle comprised of a poorly water soluble agricultural active ingredient, wherein the agricultural active ingredient is at least one herbicide selected from the group consisting of: sulfonamide herbicides, pyridine herbicides, triazolopyrimidine herbicides, and chlorotriazine herbicides, having a volume-average diameter in a range of about 30 nm to about 500 nm; and
   b) an adjuvant, wherein the adjuvant is at least one penetrant or a non-ionic surfactant, selected from the group consisting of: a crop oil concentrate and an alkylphenol ethoxylate.

2. The composition of claim 1 further comprising inert ingredients and diluents.

3. The composition of claim 1 wherein the mesoparticle is a mesocapsule having an oil phase comprised of from about 1 to about 90 weight percent of the agricultural active ingredient at least partially included within a polymer shell.

4. The composition of claim 1 wherein the mesoparticle is a meso-matrix particle comprised of from about 1 to about 90 weight percent of the agricultural active ingredient distributed throughout a polymer matrix.

5. The composition of claim 1 wherein the mesoparticle is a meso-homogeneous particle comprised of from about 80 to about 99 weight percent of the agricultural active ingredient.

6. The composition of claim 1 wherein the agricultural active ingredient has a water solubility of less than about 1000 ppm.

7. The composition according to claim 1 wherein the adjuvant is one of a built-in adjuvant and a tank-mixed adjuvant.

8. The composition of claim 1 wherein the adjuvant is tank mixed and comprises from about 0.05 to about 5 volume percent of a dilute spray solution.

9. The composition of claim 1 wherein the adjuvant is built-in and comprises from about 1 to about 90 weight percent of an aqueous or non-aqueous formulation concentrate.

10. The composition of claim 1 wherein the non-ionic surfactant is a nonylphenol ethoxylate.

11. The composition of claim 1 further comprising a conventionally formulated agricultural active ingredient.

12. A method of controlling insects, mites, plant diseases or weeds including the steps of:
providing a formulation including the composition of claim 1, and
applying an agriculturally effective amount of the formulation to at least one of the following: the plant, plant foliage, blossoms, stems, fruits, the area adjacent to the plant, soil, seeds, germinating seeds, roots, liquid and solid growth media, and hydroponic growth solutions.

13. A method of controlling insects, plants diseases or weeds including the steps of:
providing a formulation including the composition of claim 1, and
applying an agriculturally effective amount of the formulation in mixture with one or more conventional formulations of agricultural active ingredients or nutrients to at least one of the following: the plant, plant foliage, blossoms, stems, fruits, the area adjacent to the plant, soil, seeds, germinating seeds, roots, liquid and solid growth media, and hydroponic growth solutions.

14. The composition of claim 1 wherein the agriculturally active ingredient is a triazole fungicide selected from the group consisting of cyproconazole, difenoconazole, epoxiconazole, fenbuconazole, fluquinconazole, flutriafol, ipconazole, metconazole, myclobutanil, propiconazole, prothioconazole, tebuconazole, tetraconazole, triadimefon, triadimenol and triticonazole.

15. The composition of claim 1, wherein the herbicide is atrazine.

16. The composition of claim 1, wherein the herbicide is a pyridine herbicide selected from the group consisting of aminopyralid, clopyralid, fluroxypyr, picloram, and triclopyr.

17. The composition of claim 1, wherein the agricultural active ingredient is pyroxsulam and the adjuvant is selected from the group consisting of a crop oil concentrate and a nonylphenol ethoxylate.

18. The composition of claim 1, further comprising an aqueous phase, wherein the composition is an emulsion or suspension of the mesoparticle in the aqueous phase.

19. The composition according to claim 1, wherein the agricultural active ingredient is at least one herbicide selected from the group consisting of: atrazine, aminopyralid, clopyralid, fluroxypyr, picloram, triclopyr, cloransulam, diclosulam, florasulam, flumetsulam, metosulam, penoxsulam, and pyroxsulam.

* * * * *